United States Patent [19]
Guiseppi-Elie

[11] Patent Number: 5,766,934
[45] Date of Patent: Jun. 16, 1998

[54] CHEMICAL AND BIOLOGICAL SENSORS HAVING ELECTROACTIVE POLYMER THIN FILMS ATTACHED TO MICROFABRICATED DEVICES AND POSSESSING IMMOBILIZED INDICATOR MOIETIES

[76] Inventor: Anthony Guiseppi-Elie, 1273 Quarry Commons Dr., Yardley, Pa. 19067-4032

[21] Appl. No.: 318,494

[22] Filed: Oct. 4, 1994

Related U.S. Application Data

[63] Continuation-in-part of Ser. No. 771,759, Oct. 4, 1991, Pat. No. 5,352,574, which is a continuation of Ser. No. 322,670, Mar. 13, 1989, abandoned.

[51] Int. Cl.$^6$ .................................................. G01N 27/26
[52] U.S. Cl. ...................... 435/287.9; 435/817; 204/403; 204/418
[58] Field of Search .................... 435/287.7, 287.8, 435/287.9, 817; 204/403, 414, 415, 416, 418

[56] References Cited

U.S. PATENT DOCUMENTS

| | | | |
|---|---|---|---|
| 5,310,469 | 5/1994 | Cunningham et al. | 204/403 |
| 5,352,574 | 10/1994 | Guiseppi-Elie | 435/4 |

*Primary Examiner*—David A. Redding
*Attorney, Agent, or Firm*—Duane, Morris & Heckscher

[57] ABSTRACT

Chemical and biological sensors are provided that convert the chemical potential energy of an analyte into a proportionate electrical signal through the transducer action of a microfabricated device with an integral electroconductive polymer film. The microsensor devices possess a coplanar arrangement of at least one, and typically three, microfabricated interdigitated microsensor electrode arrays each with line and space dimensions that may range from 2–20 μm and is typically 10 μm, a platinized platinum counter electrode of area at least 10 times the area of the interdigitated microsensor electrode array and a chloridized silver/silver chloride reference electrode. Chemical and biological sensors constructed according to the present invention employ a thin electrically conducting polymer film that is specifically attached via covalent bond formation to the interdigitated microsensor electrode component of the devices. The electrically conducting polymer film is formed in three layers, the first layer possesses high electrical conductivity and is covalently attached to the device surface, the second layer possess an inorganic catalyst and is covalently attached to the first, and the third layer possesses an indicator molecule which may be a bioactive molecule such as an enzyme or member of specific binding pair of biological origin and is itself covalently attached to the second layer. Binding of an analyte or member of the specific binding pair reagent may result in a change in the electrical impedance (resistance and capacitance or both) of the highly electrically conducting layer. The electrical change in the polymer layers is a sensitive measure of the extent of binding of the binding agent and forms an analytical signal for the binding agent.

14 Claims, 15 Drawing Sheets

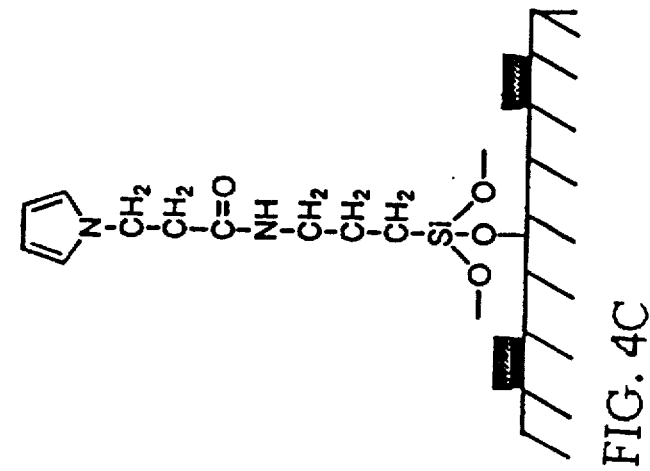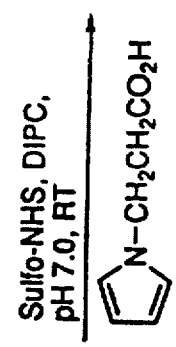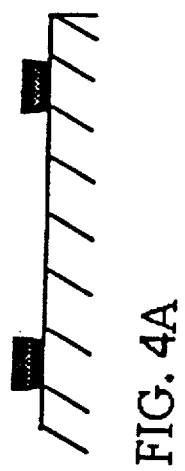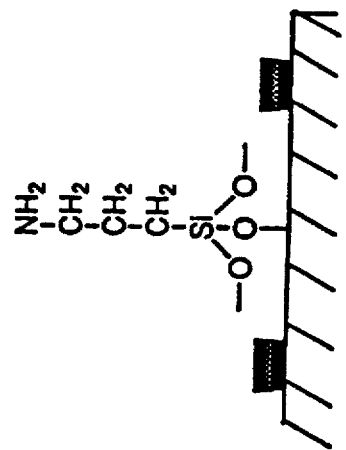
FIG. 4A  FIG. 4B  FIG. 4C

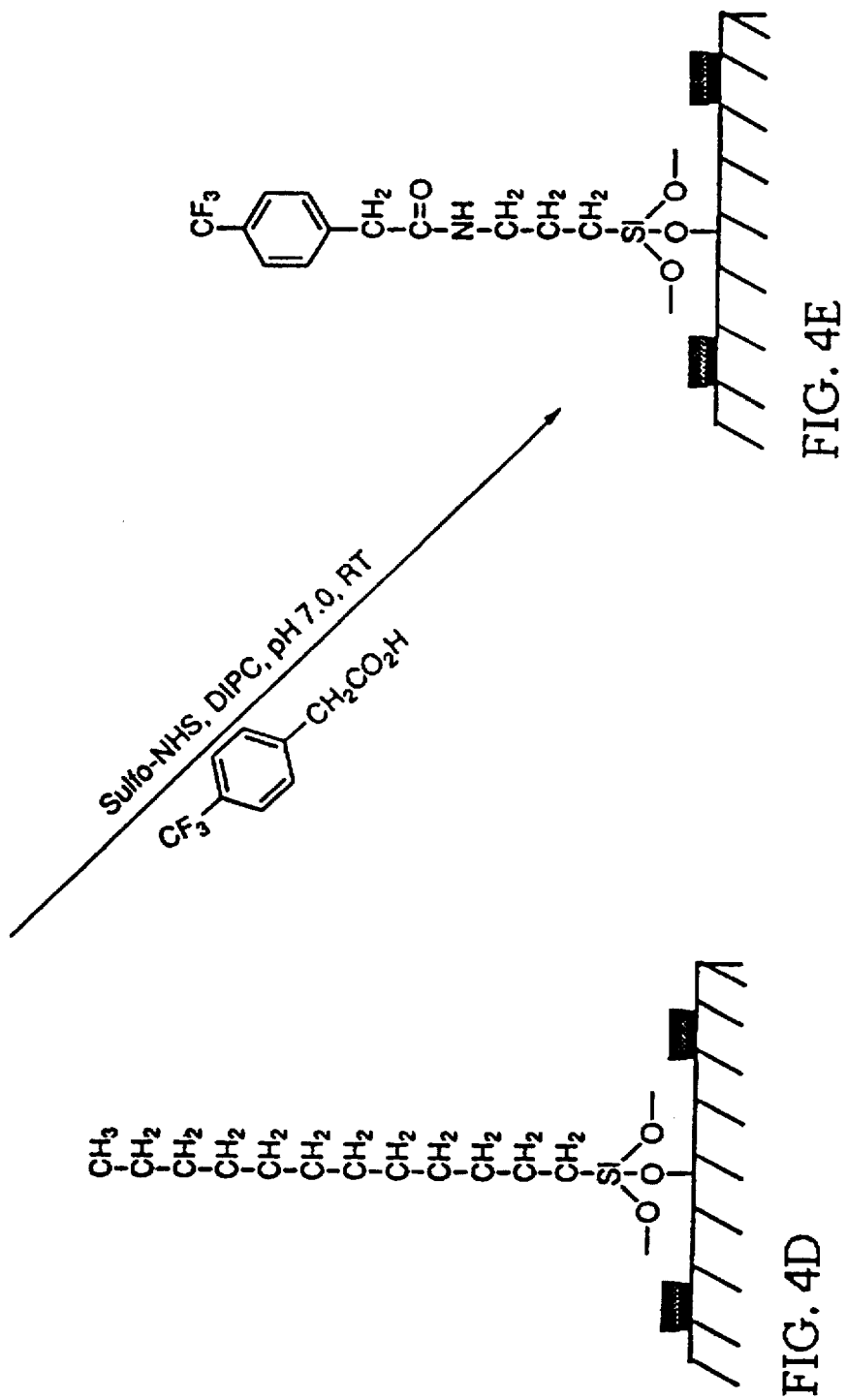

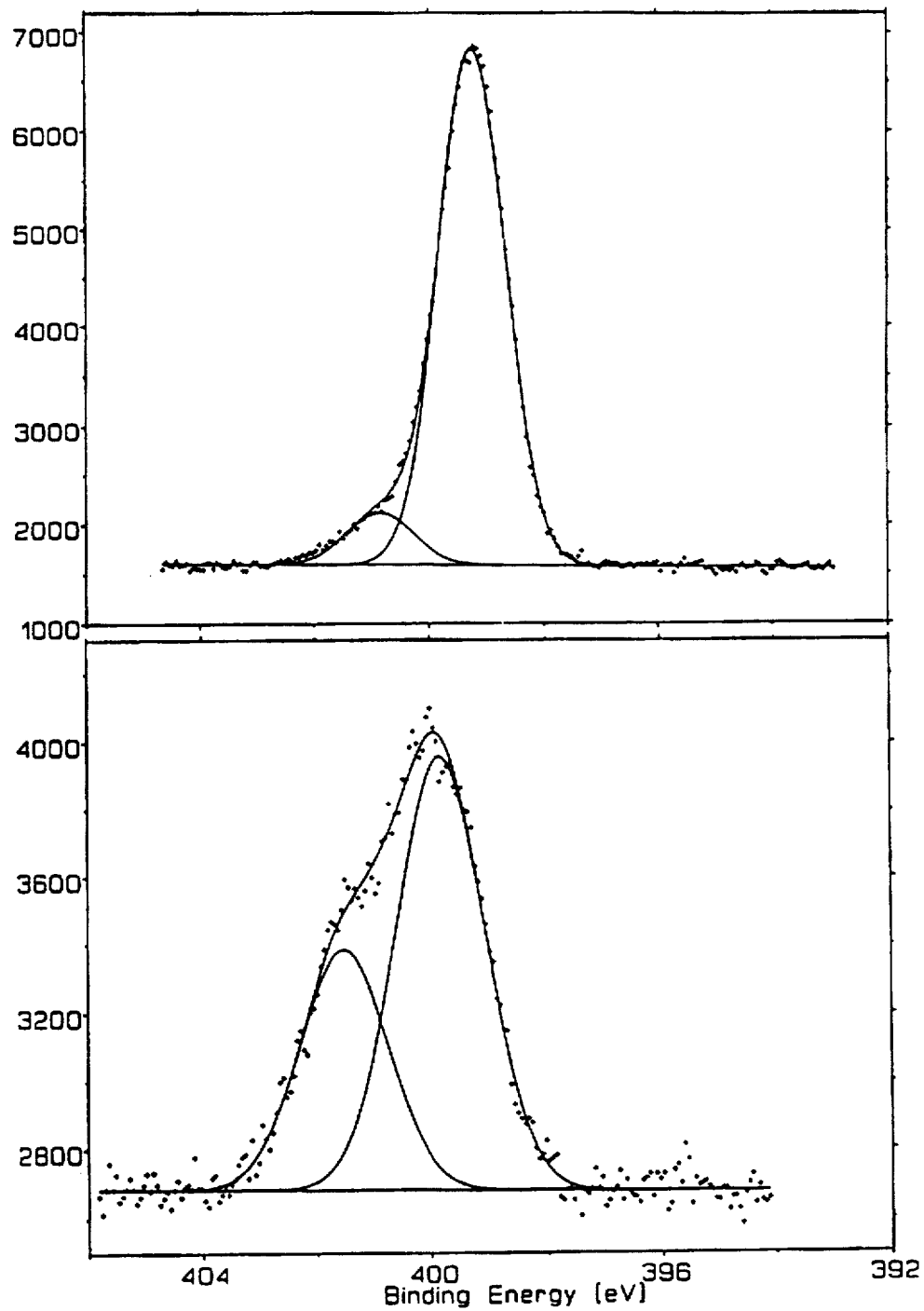

5,766,934

CHEMICAL AND BIOLOGICAL SENSORS HAVING ELECTROACTIVE POLYMER THIN FILMS ATTACHED TO MICROFABRICATED DEVICES AND POSSESSING IMMOBILIZED INDICATOR MOIETIES

RELATED APPLICATION AND CLAIM OF PRIORITY

This application is a continuation-in-part of U.S. Pat. No. 5,352,574 which issued on Oct. 4, 1994 and matured from U.S. application Ser. No. 07/771,759 which was filed on Oct. 4, 1991, which is itself a continuation of U.S. Ser. No. 322,670 filed on Mar. 13, 1989, now abandoned.

BACKGROUND OF THE INVENTION

The present invention is a conductimetric chemical sensor and or biosensor and process for its fabrication.

This invention is in the general area of chemical and biological microsensor devices and is specifically directed at materials, processes, and products derived from the covalent attachment of electropolymerized and electroconductive polymer thin films grown on microfabricated electrode devices. This invention is also directed to methods and processes for the specific immobilization of electroconductive polymer thin films onto the surface of microfabricated devices of glass or oxidized silicon. This invention is further directed to sensor devices formed from several layers of electroconductive polymers wherein the layers perform different functions within the sensor. This invention is also directed to the application of these sensors to the detection and measurement of analyte concentrations.

There is need for stable, reversible conductimetric, amperometric, voltammetric, and potentiometric chemical and biological sensor devices that respectively result from the large change in electrical impedance, the appreciable reduction in overpotential for electrochemical discharge under fixed electrode potential conditions, and the reproducible changes in open-circuit electrode potential that accompanies changes in the redox composition of electroconductive polymers. The development of chemical and biological sensor devices that are based on electroconductive polymers is an area that has attracted considerable recent attention [a) Guiseppi-Elie, A. U.S. Pat. Ser. No. 07/771,759 Electroactive Polymers with Immobilized Active Moieties. b) Umaña, M.; Waller, J.; Anal. Chem. 1986, 58, 2979–2983. c) Foulds, N. C.; Lowe, C. R. J. Chem. Soc., Faraday Trans. 1 1986, 82, 1259–1264. d) Iwakura, C.; Kajiya, Y.; Yoneyama, H. J. Chem. Soc., Chem. Commun. 1988, 15, 1019. e) Matsue, T.; Kasai, N.; Narumi, M.; Nishizawa, M.; Yamada, H.; Uchida, I. J. Electroanal. Chem. Interfacial Electrochem. 1991, 300, 111–117. f) Malmrol, M. U.S. Pat. Nos. 4,334,880 and 4,444,892 Analytic Device Having Semiconductive Organic Polymeric Element Associated with Analyte-Binding Substance. g) Malmors, M. K.; Gulbinski, III, J.; Gibbs, Jr. W. B. Biosensors, 1987/88, 3, 71.]. Sensor devices that exploit the transducer-active responses of electroactive polymers such as polypyrrole, polyaniline, and polythiophene may be conductimetric [a) Lawrence, A. J.; Moores, G. R. Europ. J. Biochem. 1972, 24, 538–546. b) Cullen, D. C.; Sethi, R. S.; Lowe, C. R. Anal. Chim. Acta 1990, 231, 33–40.] when they use the large change in electrical impedance [a) Guiseppi-Elie, A.; Wilson, A. M. Proceedings 64th Colloid and Surf Sci. Symp., Jun. 18–20, 1990. Leigh University, Lehigh, Pa. b) Matsue, T.; Nishizawa, M.; Sawaguchi, T.; Uchida, I. J. Chem. Soc., Chem. Commun. 1991, 1029–1031. c) Nishizawa, M.; Matsue, T.; Uchida, I. Anal. Chem. 1992, 64, 2642–2644. d) Hoa, D. T.; Kumar, T. N. S.; Punekar, N. S.; Srinivasa, R. S.; Lal, R.; Contractor, A. Q. Anal. Chem. 1992, 64, 2645–2646. e) Guiseppi-Elie, A. U.S. Pat. No. 5,312,762 Method of Measuring an Analyte by Measuring Electrical Resistance of a Polymer Film Reacting with the Analyte.] that accompanies oxidation and or reduction of the polymer, amperometric [Gorton, L.; Bremle, G.; Csöregi, E.; Jönsson-Pettersson, G.; Presson, B. Anala. Chim. Acta 1991 249 43–54.] when they use redox mediation and or electrocatalysis [a) Gholamian, M.; Sundaram, J.; Contractor, A. Q. Langmuir, 1987, 3, 741. b) Kajiya, Y.; Sugi, H.; Iwakura, C.; Yoneyama, H. Anal. Chem. 1991, 63, 49. c) Sun. Z.; Tachikawa, H. Anal. Chem. 1992, 64, 1112–1117.], or potentiometric [a) Dong, S.; Sun, Z.; Lu, Z. J. Chem. Soc.; Chem. Commun. 1988, 993. b) Dong, S.; Sun, Z.; Lu, Z. Analyst 1988, 113, 1525. c) Lu, Z.; Sun, Z.; Dong, S.; Electroanalysis, 1989, 1, 271. d) Karagözler, A. E.; Ataman, O. Y.; Galal, A.; Xue, Z-L.; Zimmer, H.; Mark, Jr., H. B. Anala. Chim. Acta 1991 248 163–172. e) Ma, Y. L.; Galal, A.; Zimmer, H.; Mark, Jr., H. B.; Huang, Z. F.; Bishop, P. B. Anala. Chim. Acta 1994 254 163–172] when they use the electrode potential change that accompanies changes in polymer redox composition. In general, these devices are formed from thin films of the electroconductive polymer fabricated on a pattern of microsensor electrodes formed on an insulating substrate.

Conductimetric enzyme biosensors that are based on (i) the generation of ionic groups (e.g. the amidases) or (ii) the separation of unlike charges (e.g. the decarboxylases) tend to be rather poorly selective because all charge-carrying species of the sample, including background species, are detected simultaneously. Biosensors that use this principle must be operated in low ionic strength media since the detection limit is determined by the ratio $\Delta G/G$, where $\Delta G$ is the enzymatically generated change in conductance and $G$ is the background conductance of the medium. The use of electroconductive polymers that are at one time and under one set of conditions, poor electrical and ionic conductors, and at another, highly electronically and ionicly conducting, makes it possible to perform conductimetric analyses in sample matrices where the background conductance is high. This eliminates the limitation that conductimetry be performed in low ionic strength media. These materials also provide a convenient means to confer selectivity and specificity to conductimetric analyses.

Electropolymerization provides a unique and convenient method of polymer film fabrication for such devices as it confers the following major advantages: i) control of the location of the polymer film leading to micropatterning of the organic polymer on the device, ii) direct association of the polymer with metallic or semiconductor electrodes for device interrogation and signal capture, iii) precise control of polymer film thickness by control of the electropolymerization charge density [Guiseppi-Elie, A.; Pradhan, S. R.; Wilson, A. M.; Allara, D. L.; Zhang, P.; Collins, R. W.; Kim, Y.-T. Chem. Mater. 1993, 5(10), 1474–1480.], and iv) convenient device functionalization by electrophoretic blending with other molecules that confer chemical and biological specificity to the device. Such molecules may be of biological origin such as polypeptides [Prezyna, L. A.; Qui, Y-J.; Reynolds, J. R.; Wnek, G. E. Macromolecules 1991, 24, 5283.], enzymes [a) Sun, Z.; Tachikawa, H. In Biosensors and Chemical Sensors: Optimizing Performance Through Polymeric Materials; Edelman, P. G.; Wang, J., Eds.; ACS Symposium Series, 487; American Chemical Society: Washington D.C., 1992, Chapter 11, pp 134–149. b) John, R.;

Spencer, M.; Wallace, G. G.; Smyth, M. R. *Anala Chim. Acta.* 1991, 249 381–385.], cofactors [Hepel, M.; Dentrone, L.; Seymour, E. In *Polymer Solutions, Blends and Interfaces*; Noda, I. and Rubingh, D. N. Eds. Elsevier Science Publishers: New York, N.Y. 1992, pp 385–405.], antibodies, or may be inorganic catalysts such as heteropolyanions [Bidan, G.; Genies, E. M.; Lapkowski, M. *J. Chem. Soc, Chem. Commun.* 1988, 533.], semiconductor particles [Hepel, M.; Seymour, E.; Yogev, D.; Fendler, J. H. *Chem. Mater.* 1992, 4(1), 209–216.], or metallic inclusions [Wrighton et al. U.S. Pat. No. 4,717,673].

During potentiostatic electropolymerization, the PPy film is grown at a fixed potential selected to induce charge transfer initiation of the monomer as well as growth and deposition of the polymer film. However, since the polymer generally has an oxidation potential that is lower than that of its monomer, the polymer is consequently grown under continuously oxidizing conditions leading to incorporation of counteranions. One major technological limitation to the development of viable chemical and biological sensor devices based on electroconductive polymers has been the poor adhesion of electroconductive polymers to device surfaces. Recently, Nishizawa et al. [Nishizawa, M.; Miwa, Y., Matsue, T.; Uchida, I. *J. Electrochem. Soc.* 1993, 140 (56), 1650.] reported on the use of surface pretreatment to facilitate lateral growth of polypyrrole films onto and between gold microband electrodes. Yon-Him et al. [Yon-Hin, B. F. Y.; Smolander, M.; Crompton, T.; Lowe, C. R. *Anal. Chem.* 1993, 65, 2067–2071.] have also demonstrated the co-electropolymerization of 1-pyrrolyl functionalized glucose oxidase leading to specific attachment of active GOx within electropolymerized polypyrrole films. These works address scientific issues of technological significance to chemical and biosensor devices based on electroconductive polymers. In this patent we disclose and describe a unique and novel sensor device configuration comprising microfabricated devices possessing a coplanar arrangement of at least one, and typically three, microfabricated interdigitated microsensor electrode arrays each with line and space dimensions that may range from 2–20 µm and is typically 10 µm, a platinized platinum counter electrode of area at least 10 times the area of the interdigitated microsensor electrode array and a chloridized silver/silver chloride reference electrode. In this patent we also disclose and describe the development of a simple chemical modification and derivatization scheme to promote specific adhesion of electropolymerized polypyrrole and other electroconductive polymer films formed on interdigitated microsensor electrode (IME) arrays of gold on borosilicate glass and/or oxidized silicon. We further disclose and describe in this patent how these electroconductive polymer films may be rendered chemically and biologically specific to various analytes.

Electroconductive polymers are expected to play a significant role as transducer-active materials in various forms of chemical and biological sensor devices. For example, U.S. patent application Ser. No. 07/771,759 "Electroactive Polymers With Immobilized Active Moieties" discloses and describes several electropolymerized polymers in which the polymeric material is conferred with chemical or biological specificity through the covalent attachment or specific immobilization of other chemically active and biologically active moieties or indicator agents to the polymer. Examples of these electropolymerized and electroconductive polymers include the polypyrroles, the polyanilines and the polythiophenes. Specific examples of these polymers include polypyrrole, poly(N-butylpyrrole), polyaniline, poly(N-butylaniline), polythiophene, and poly(3-butylthiophene). Thus, "when an analyte in a sample reacts with the indicator reagent, electrical conductivity of the polymer is changed and the presence of the analyte is indicated by the change in electrical conductivity". Methods disclosed and described for the attachment of indicator reagents to the polymer include i) surface chemical modification, functionalization and derivatization of pre-formed polymer films, ii) chemical modification, functionalization and derivatization of electropolymerizable monomer followed by co-electropolymerization with non-functionalized monomer, and iii) electrophoretic blending of the indicator reagent with the electropolymerized polymer during electropolymerization.

A further example is U.S. Pat. No. 5,312,762 "Method of Measuring an Analyte by Measuring Electrical Resistance of a Polymer Film Reacting with the Analyte" which discloses and describes procedures for a method of analysis and associated instrumentation for using the foregoing polymer materials as sensors by obtaining chemically based or biologically based electrical signals from sensors formed from these electropolymerized and electroconductive polymers. The teachings of the two foregoing applications are all specifically incorporated herein by reference.

U.S. Pat. No. 4,721,601 (Wrighton et al.), U.S. Pat. No. 4,895,705 (Wrighton et al.) and U.S. Pat. No. 5,034,192 (Wrighton et al.) disclose electropolymerization as a method for the deposition of electroconductive polymer films on microfabricated devices. Methods and procedures for the specific attachment by covalent immobilization of the electropolymerized polymer are absent in these patents. Furthermore, these patents fail to disclose methods and procedures to confer chemical and biological specificity to sensors formed with electroactive polymers. Thus devices when fabricated from electroconductive polymers via the process of electropolymerization according to the procedures of U.S. Pat. Nos. 4,721,601, 4,895,705, and, 5,034,192 make no attempt to bond or attach the polymer film to the device. Such polymers should be bonded to the device if the device is to have long term stability and to resist delamination upon prolonged immersion in aqueous, humid or other aggressive environments. It is the object of this invention to provide for microsensor devices formed via microfabrication techniques and possessing integral electroconductive polymers that are grown by electropolymerization and in which the electroconductive polymer is covalently attached to the device. It is a further object of the present invention to provide methods, materials and procedures for making such a covalently attached electroconductive polymer film on a microsensor device.

U.S. Pat. No. 5,312,762 (Guiseppi-Elie) describes procedures for extracting analytically significant data from conductimetric sensors that have chemically sensitive electroconductive polymer thin films grown or deposited on microfabricated interdigitated microsensor electrodes. The sensor of U.S. Pat. No. 5,312,762 (Guiseppi-Elie) uses an externally placed, free-standing auxiliary or counter electrode and an externally placed, free-standing silver/silver chloride reference electrode. As a consequence, the sensor of U.S. Pat. No. 5,312,762 (Guiseppi-Elie) cannot be conveniently configured into a low cost, convenient, and disposable sensor cartridge suitable for one-time field use. The object of this invention is to provide a sensor device wherein all the electrode elements are microfabricated directly onto the same sensor chip thereby eliminating the need for an externally placed, free-standing reference electrode and an externally placed, free-standing auxiliary or counter electrode. Such a sensor may be readily fabricated as a convenient, low cost, disposable sensor suited to field use.

SUMMARY OF THE INVENTION

In accordance with the present invention, a sensor comprising a microfabricated chip comprising at least one interdigitated microsensor electrode array, a first electrode of platinized platinum, and a second reference electrode, said first electrode and second reference electrode being coplanar on the chip with said array, said chip further comprising, an interdigit area that is chemically modified and derivatized to promote adhesion over said interdigitated electrode array, a first layer of electroactive polymer material formed over the interdigit area, and being covalently attached, adhered, and contiguous with the interdigit area of the chip, a second layer of electroactive polymer material, including an inorganic catalyst, formed over said first electroactive polymer layer, and a third layer of electroactive polymer material, including an indicator agent, formed over said second electroactive polymer layer.

Chemical and biological sensors are provided comprising i) a microfabricated silicon or glass chip possessing a coplanar arrangement of at least one, and typically three, microfabricated interdigitated microsensor electrode arrays each with line and space dimensions that may range from 2–20 µm and is typically 10 µm, a platinized platinum counter electrode of area at least 10 times the area of the interdigitated microsensor electrode array, and a chloridized silver/silver chloride ($Ag^°/AgCl$) reference electrode, ii) an interdigit area of the chip that is chemically modified using a functional silane and the silane subsequently derivatized with an electropolymerizable monomer of pyrrole, thiophene or aniline, iii) an electropolymerized layer of highly electrically conducting polypyrrole, polythiophene or polyaniline formed over the interdigit area that is covalently attached, adherent, and fully contiguous over the interdigit area of the chip, iv) a subsequent layer of electropolymerized polymer possessing an inorganic catalyst, v) a third layer of electropolymerized polymer possessing an indicator agent such as an enzyme, or member of a specific binding pair reagent. Reaction of an analyte in a sample with the immobilized indicator reagent changes the electrical conductivity of the polymer layers. The presence of the analyte is indicated by the change in the electrical conductivity and the concentration of the analyte is indicated by the rate of change and the extent of change of the electrical conductivity of the device.

In one embodiment, a 4"×4" insulating glass plate (Schott D 262) is solvent cleaned, surface activated in "piranha" etch (1:1, $H_2O_2/H_2SO_4$), plasma cleaned, and then magnetron sputtered with a 100 Å layer of titanium/tungsten (Ti/W) followed by 1,000 Å layer of gold (Au) or platinum (Pt). The plate is then patterned using standard microfabrication techniques to yield individual die called prototransducers, each possessing three interdigitated areas, a metallized area that is 10 times the area occupied by the interdigitation, and another metallized area roughly equal in area to the interdigitation. Each interdigit area typically comprises ten (10) opposing line pairs but may be 2 to 50 line pairs, each line or digit is typically 3 mm long but may be 1 mm to 5 mm long, and typically possesses 10 µm line and space dimensions that may be 2 µm. to 20 µm. These interdigit areas serve as the sites for the growth and/or deposition of the electoconductive polymer film that confers onto the prototransducer chip its chemically responsive properties.

In a second embodiment, the interdigit areas of the prototransducer chip are chemically modified with an amino silane such as 3-aminopropyltrimethoxysilane. This converts the chemistry of the borosilicate glass surface to the chemistry of the organosilane. The 10 µm spaces are derivatized by chemical modification with 3-aminopropyltrimethoxysilane followed by direct linking of the 1° amine of the organosilane to the carboxylic acid group of 3-(1-pyrrolyl)propionic acid. The linking is done using the heterobifunctional linker 1,3-diisopropylcarbodiimide enhanced with N-hydroxysulfosuccinimide in aqueous solution at room temperature. The use of a terminally active silane and a heterobifunctional crosslinker for specific immobilization is known [Bhatia, S. K.; Shriver-Lake, L. C.; Prior, K. J.; Georger, J. H.; Calvert, J. M.; Bredehorst, R.; Ligler, F. S. *Anal. Biochem.* 1989, 178, 408.]. In this case, however, the silane is derivatized with an electropolymerizable moiety such as 3-(1-pyrrolyl)propionic acid. This replaces the primary amine of the interdigit space with an electropolymerizable pyrrole moiety in the omega position. The 3-(1-pyrrolyl) propionic acid is disclosed herein to be electroactive, electropolymerizable, and co-electropolymerizable with pyrrole under the conditions commonly used for the electropolymerization of pyrrole. Electroconductive PPy films grown on these ω-(1-pyrrolyl) derivatized IME prototransducer devices were allowed to bridge the interdigit space and so be co-electropolymerized with ω-(1-pyrrolyl) moieties specifically attached to the interdigit space of the device. This leads to specific attachment of the electropolymerized PPy film to the surface of the device. Films grown in this way were compared to films similarly grown on unmodified IME devices, on IME devices rendered hydrophobic by chemical modification with the n-alkylsilane—dodecyltrichlorosilane, and on devices modified with 3-aminopropyltrimethoxysilane —the precursor to ω-(1-pyrrolyl) derivatization. The chemical surface modification of the interdigit space of the device had only a modest but noteworthy influence on the electropolymerization kinetics. PPy films grown on unmodified glass surfaces required the longest electropolymerization time of ca. 23 min. Films grown on aminopropyltrimethoxysilane-modified surfaces required the shortest electropolymerization time of ca 16 min. The electropolymerization time for the polypyrrole films grown on the various surfaces was observed to occur in the order; unmodified surface (23.2 min.)>>dodecyltrichlorosilane-modified surface (18.0 min.)>ω-(1-pyrrolyl) derivatized surface (17.2 min.)>3-aminotrimethoxysilane-modified surface (16.1 min.). It is arguable that there is essentially no difference in the polymerization kinetics arising from the various substrate surface chemistries, however, these differences were reproducible and possibly reflect the relative ease with which pyrrole monomer may be adsorbed to the interdigit space to promote lateral electropolymerization. Films were electropolymerized such that they completely bridged the interdigit space and formed a fully contiguous layer over the active device surface. In this way electrochemical, electrical, and adhesion measurements could be made on the film. Films grown on ω-(1-pyrrolyl) derivatized IME devices and on 3-aminopropyltrimethoxysilane modified surfaces display some modest variation in electroactivity as measured by cyclic voltammetry but are otherwise the same. PPy films grown on ω-(1-pyrrolyl) derivatized IME devices display significantly enhanced adhesion compared to films grown on any of the other surfaces studied. Films readily pass the Scotch® tape test and did not disbond after six months of continuous immersion in PBS 7.2 buffer or when maintained dry under vacuum and over molecular sieves. This is to be compared to unmodified IME devices and dodecylsilane modified IME devices from which the film fails the Scotch® tape test and readily disbonded after 3 days and after 5 days of immersion in PBKCl pH 7.2 buffer respectively. The time to adhesive failure in both test environments occurred in the order unmodified<dodecyltrichlorosilane modified <<3-aminotrimethoxysilane modified<<ω-(1-pyrrolyl) derivatized. The failure times were 3 days<5 days<<27 days<<6 months + for films immersed in aqueous PBKCl pH 7.2 buffer and were 3 days<30 days<<6 months + <<6 months + for films stored dry and desiccated under vacuum. The combined electrochemical and adhesion test evidence suggest that the PPy films are specifically immobilized to the ω-(1-pyrrolyl) derivatized IME devices and that specific immobilization overcomes the hydrolytic instability of the PPy/glass interface under aqueous immersion conditions.

In yet a third embodiment, an electroactive polymer film of polypyrrole is anodicly electropolymerized onto the microfabricated chip from a solution of pyrrole monomer, polymeric counter anion, anionic surfactant additive, leveling aids and inorganic and organic additives. The polymer film is grown such that the film bridges the interdigit space between the digits, is copolymerized with the immobilized electropolymerizable monomer that is covalently attached to the surface, and is accordingly itself covalently attached to the surface of the chip. The result is a highly adherent and fully contiguous film of electroconductive polymer spanning the interdigit space of the chip. Membrane films were grown by potentiostatic electropolymerization onto the IME component of prototransducer chips with interdigit spaces that were modified with 3-aminopropyltrimethoxysilane and conjugated with 3-(1-pyrrolyl)propionic acid using N-hydroxysulfosuccinimide (sulfo-NHS) (Pierce) and 1,3-diisopropylcarbodiimide (DIPC) (Chemical Dynamics). The ω-(1-pyrrolyl) derivatized devices were held at a potential of +0.65 V vs. Ag°/AgCl, 3M Cl⁻(RE803, AAI-ABTECH) applied to the combined/shorted electrodes of the IME component using an EG&G PAR 173 Potentiostat/Galvanostat and PAR 179 Digital Coulometer. The film grew on each electrode and also between the digits of the pair of electrodes such that it formed an adherent and fully contiguous membrane on the device. The film was grown from three (3) different electropolymerization baths to form a three-layer laminate membrane. The first was a highly conducting layer that was specifically attached via surface copolymerization with immobilized ω-pyrrole moieties. The second was a catalyst carrying layer and the third layer an enzyme carrying layer. The first electropolymerization bath contained 0.2M pyrrole (Py), 2.5 mM poly(styrenesulfonic acid) (PSSA), 2.5 mM sodium dodecylbenzenesulfonate (DBS) and 0.1 mM mercaptopropionic acid (MPA) at a pH of 3.0 and at a constant T=20° C. Films were grown to a total anodic electropolymerization charge density, $Q_e$, of $2.00 \times 10^{-2}$ C/cm². These first layer films are highly electrically conducting with a conductivity of ca. $1 \times 10^{-2}$ S/cm, are chemically responsive and are fully adherent to the device surface. The second and catalytic polymer layer was similarly prepared to a total anodic electropolymerization charge density, $Q_e$, of $2.00 \times 10^{-2}$ C/cm² from an electropolymerization bath that was similar to that used for the first layer but was neutralized by the dropwise addition of 0.015% polyvinylamine (PVAm) and also contained 1 mg/ml poly(1-lysine) and 0.1 mM $Mo_7O_{24}^{6-}$ ($Mo^{VI}$). These second layer films carry the $Mo^{VI}$ catalyst which is incorporated into the film as it is formed. The third and biospecific polymer layer was similarly prepared to a total anodic electropolymerization charge density, $Q_e$, of $2.00 \times 10^{-2}$ C/cm², from an electropolymerization bath that was similar to that used for the first layer but like the second layer was neutralized by the dropwise addition of 0.015% polyvinylamine (PVAm). This third layer was formed from a bath that also contained 1 mg/ml of the enzyme glucose oxidase. These third layer films contain the biospecific agent glucose oxidase which makes the resulting sensor sensitive to glucose.

BRIEF DESCRIPTION OF THE DRAWINGS

FIGS. 4A, 4B, 4C, 4D and 4E. Schematic illustration of the various steps in the preparation of the various chemically modified surfaces of the interdigitated microsensor electrode (IME) component of the prototransducer device showing A) unmodified surface, B) aminosilanized surface, C) 3(1-pyrrolyl)propionic derivatized surface, D) dodecylsilanized surface, and E) (ααα-trifluro-p-tolyl)acetic acid derivatized surface.

FIGS. 5A and 5B. XPS spectra of the N1s region of A) aminosilanized, B) 3(1-pyrrolyl)propionic derivatized device surfaces.

DESCRIPTION OF THE SPECIFIC EMBODIMENTS

The present invention is directed to chemical sensors and biological sensors for the detection and measurement of analytes. The chemical and biological sensors of the present invention are formed by the microfabrication of a pattern of metallic electrodes on an insulating substrate chip called a prototransducer. The prototransducer is microfabricated from oxidized silicon or glass chips possessing inert interdigitated array electrodes of gold or platinum, a counter or auxiliary electrode of platinized platinum, and a reference electrode of silver/silver chloride (Ag°/AgCl) that are all coplanar on the chip. A transducer is formed from the prototransducer by the growth or deposition of a chemically responsive, organic, polymeric film over the electrodes of the interdigitated microsensor electrode array element of the prototransducer. The polymer film is electroconductive and is drawn from the family of polymers such as the polyanilines, polypyrroles, and the polythiophenes. The transducer is converted into a chemical or biological sensor when the electroconductive polymer film of the transducer is rendered specific to a given analyte of chemical or biological origin by the covalent immobilization onto the transducer of an inorganic, organic or biological indicator molecule that is specific to that analyte.

Figure 1A:
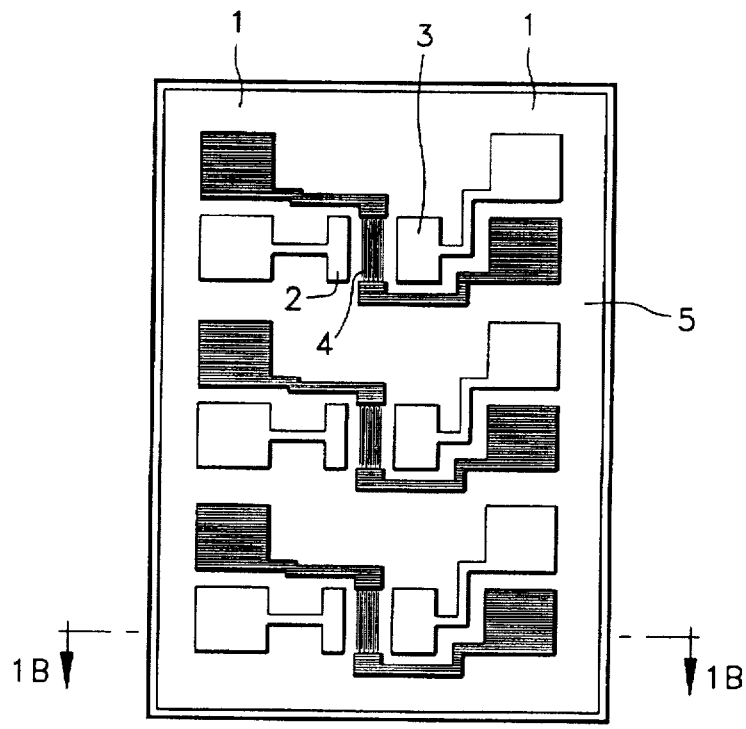
FIGS. 1A 1B 1C. A schematic illustration of A) the plan view, and B) the sectional view through the line B—B and C an isolated view of a microfabricated chemical or biological sensor device showing the bonding pads (1), silver/silver chloride reference electrode (2), platinized platinum electrode (3), and the interdigit area (4) on the insulating substrate (5).
Figure 1B:
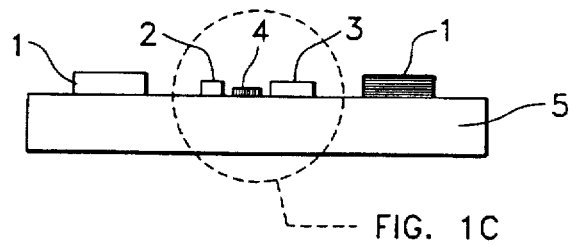
Figure 1C:
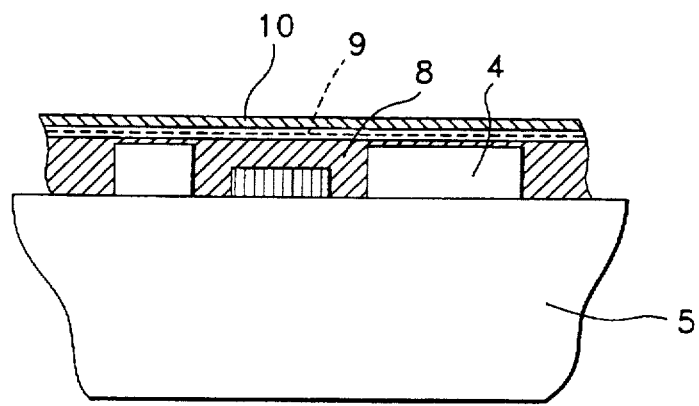

FIGS. 1A through 1C are respective plan section and isolated views of a preferred sensor in accordance with the present invention. The sensor comprises binding pads 1. In a most preferred embodiment, a silver/silver chloride reference electrode 2 is connected to pads 1. In a preferred embodiment, the platinized platinum electrode 3 is co-plated with the reference electrode 2 and an interdigitated microsensor array 4. A first layer covalently attached, adhered to and contiguous with the interdigit area. A second catalytic layer 9 is former over layer 8. A third layer of electroactive polymer 10 including an indicator agent is formed over the second polymer layer. In a most preferred embodiment, item 11 is an immobilized biotin molecule, 12 is a bound streptavidin molecule and 13 is a bound biotinylatd glucose oxidase molecule.

Prototransducer Design

The individual microfabricated prototransducer chip consisted of a coplanar arrangement of at least one, and typically three, microfabricated interdigitated microsensor electrode arrays, a platinized platinum counter electrode of area at least 10 times the area of the interdigitated microsensor electrode array, and a chloridized silver/silver chloride (Ag°/AgCl) reference electrode. The interdigitated microsensor electrode arrays on the chip consisted of digit pairs that ranged from 2 to 50 and were typically 10 digit pairs. The digits themselves had lines and spaces that ranged from 2 µm to 20 µm and were typically 10 µm wide. Each digit was typically ca. 3 mm (2.999 µm) long but was varied from ca 5 mm to ca 1 mm. The total interdigit area of the interdigitated array of the prototransducer device was typically 0.0117 cm$^2$ on a chip that was ca 1.0 cm×2.5 cm. Table 1 shows the various dimensions and calculated parameters associated with the interdigitated array component of the microfabricated prototransducer chip.

The platinized platinum component of the chip varied in area depending on the line width of the digits and was typically ten (10) times the area of the interdigitated microsensor electrode array. The silver/silver chloride electrode also varied in area depending on the line width of the digits and was typically equal to the area of the interdigitated microsensor electrode array. The platinized platinum and silver/silver chloride electrodes were placed on opposite sides and so bracketed the interdigitated microsensor electrode array.

TABLE 1

Critical dimensions and parameters associated with the interdigitated array component of the prototransducer.

| | | | | |
|---|---|---|---|---|
| Digit Width, a, (µm): | 20 | 15 | 10 | 05 |
| Digit length, d, (µm): | 2,980 | 2,985 | 2,990 | 2,995 |
| No. of digit pairs, N: | 10 | 10 | 10 | 10 |
| Interdigit Space, a, (µm): | 20 | 15 | 10 | 05 |
| Spatial Periodicity, λ, (µm) | 80 | 60 | 40 | 20 |
| Zaretsky$^{a,b}$ Meander Length, M, (cm) | 29.99 | 29.99 | 29.99 | 29.99 |
| Serpentine Length$^c$, S, (cm) | 57.20 | 57.20 | 57.20 | 57.20 |
| Cell Constant$^d$, K, (cm$^{-1}$) | 0.033 | 0.033 | 0.033 | 0.033m |
| Interdigit Area$^e$, A, (cm$^2$) | 0.0234 | 0.0176 | 0.0117 | 0.0059 |

$^a$Zaretsky, M. C.; Mouyad, L.; Melcher, J. R. IEEE Trans. Electr. Insul. 1988, 23, 897.
$^b$The Zaretsky convention defines the Meander length; M = N · d
$^c$The Serpentine Length, S = d(2N − 1) + 2a(2N − 2) + 3a
$^d$Sheppard, N. F.; Tucker, R. C.; Wu, C. "Electrical Conductivity Measurements Using Microfabricated Interdigitated Electrodes" Anal. Chem. 1993, 65, 1199.
$^e$The Interdigit Area, A = (a$^2$ + da) (4N − 1)

Microfabrication of Prototransducers

Prototransducer devices were fabricated in the Microfabrication Facility of SRI-David Sarnoff Research Center. This facility is contained within a class 100 clean room and is fully equipped to perform the integrated circuit fabrication procedures described. To fabricate the prototransducers, a four mask process was employed. The first mask was designed as a light-field (clear-field) mask to produce the bi-metallic interdigitated microsensor electrode arrays and the various bonding pads to the interdigitated microsensor electrodes as well as to the counter/auxiliary and reference electrodes via an ion-beam milling process. The second mask was designed to produce the platinum counter electrodes by a lift-off process. The third mask was designed to produce the silver reference electrodes by a lift-off process. The fourth and final mask was designed as a dark-field mask and was used to produce a windowed dielectric layer over the complete chip such that only the active interdigit area, the auxiliary electrode area and the reference electrode area were exposed to the external test environment.

A chemically resistant, electronics quality Schott D263 Borosilicate glass obtained from Technical Glass (PA) as 10.16 cm (4")×10.16 cm (4")×0.050 cm plates were used as solid, insulating substrates for the microfabrication of prototransducers. Other substrates such as 5.8 cm (2")×5.8 cm (2")×0.050 cm borosilicate glass plates, 4" diameter oxidized silicon wafers, 4" square lithium niobate plates were also used. Any smooth, flat, polished and insulating substrate may be used including polyimide and other plastic film substrates. Following standard substrate cleaning and activation, the prototransducers were fabricated by magnetron sputtering of 100 Å of adhesion promoting titanium/tungsten (Ti/W) or chromium (Cr) onto the substrate followed by magnetron sputtering of 1,000 Å of gold over the Cr or Ti/W in a Model VS-24C Magnetron Sputterer from Iontec Group Inc. (CA). Positive photoresist (American Hoest 1375) was syringed onto the metallized plate and spun at 4,000 rpm for 40 sec. The positive photoresist was then pre-baked at 85° C. before being exposed using the first light-field (clear-field) mask on a Model System II mask aligner from Hybrid Technology Group (CA). The photoresist was then developed (Shipley 351), leaving an exact image of the electrodes patterned in the photoresist, and the plate ion-beam milled in a Model 21-1500-750 IFC from Ion Tech, Inc. (CO). This procedure produced the three separate interdigitated microsensor electrode arrays and the various bonding pads to the interdigitated microsensor electrodes as well as to the auxiliary and reference electrodes. When the interdigit areas were required to be fabricated from platinum, the plates were metallized (100 α of adhesion promoting titanium/tungsten (Ti/W) or chromium (Cr) onto the substrate followed by electron-beam evaporation of 1,000 Å of platinum over the Cr or Ti/W) in a Model BJD-1800 electron beam evaporator from Temescal (CA).

In the second step, positive photoresist was again spun onto the previously milled plate, pre-baked, exposed to the second dark-field mask in the aligner and developed. This second pattern was a reverse image of the desired electrodes that created an open window in the photoresist where the platinized platinum electrode was to be placed. Finally the plate was metallized by electron-beam evaporation with 100 Å of adhesion promoting titanium/tungsten (Ti/W) or chromium (Cr) onto the substrate followed by 1,000 Å of platinum over the Cr or Ti/W. The plate was then ultrasonically agitated in developer to "lift-off" the unwanted metal and leave a pattern of previously formed gold interdigitated arrays and newly formed platinum counter electrodes.

In the third step, positive photoresist was again spun onto the previously milled plate, pre-baked, exposed to the third dark-field mask in the aligner and developed. This third pattern was also a reverse image of the desired electrodes that created an open window in the photoresist where the chloridized silver/silver chloride electrode was to be placed. Finally the plate was metallized by electron-beam evaporation with 100 Å of adhesion promoting titanium/tungsten (Ti/W) or chromium (Cr) onto the substrate followed by 2,000 Å of silver over the Cr or Ti/W. The plate was then ultrasonically agitated in developer to "lift-off" the unwanted metal and leave a pattern of previously formed gold interdigitated arrays, recently formed platinum counter electrodes, and newly formed silver reference electrodes.

Finally, in the fourth and final step, 4 ml of negative-acting photopolymerizable polyimide photoresist, Probimide 412 (OCG), was syringed onto the previously milled plate and spun by ramping up to 3,000 rpm and held there for 25 sec. The photoresist was pre-baked at 110° C. for 15 min. before being exposed to the fourth dark-field mask. The exposed resist was then developed and further cured by ramping from room temperature to 380° C. in 45 min., holding the temperature at 380° C. for 35 min. then cooling down to room temperature over a 2 hr. period. This produced a stable, chemically resistant, windowed dielectric layer over the complete plate such that the active elements of an interdigitated array, a platinum counter electrode, and a silver reference electrode were exposed through each window.

The exposed platinum electrodes were platinized at a current density of 59 mA/cm$^2$ in a platinizing bath that consisted of 0.01M chloroplatinic acid, 0.001M lead acetate, and 0.05% triton-X-100 in 0.02M HCl. The platinum electrodes were platinized to a total cathodic charge density of 1.12 mC/cm$^2$. The exposed silver electrodes were chloridized at a current density of 10 mA/cm$^2$ in a chloridizing bath that consisted of aqueous 0.1M KCl, 0.001M AgNO$_3$ and 0.05% triton-X-100. The silver electrodes were chloridized to a total anodic charge density 10.0 mC/cm$^2$.

Instrumentation and Equipment

Potentiostatic electropolymerization of pyrrole was carried out using an EG&G PAR 173 Potentiostat/Galvanostat outfitted with a PAR 179 Digital Coulometer. Where needed, potentiodynamic sweeps were accomplished by interfacing the PAR 173 to a PAR 175 Universal Programmer and cyclic voltammograms were recorded on an Esterline Angus XYY' 540 Recorder. Cyclic voltammetric characterization of pyrrole monomer and electropolymerized polypyrrole films was carried out using an EG&G PAR Model 273 Potentiostat/Galvanostat interfaced to an ACER 486 33MHz PC outfitted with EG&G PAR's Model 270 data acquisition and instrument control software. Electropolymerized polypyrrole films fabricated on the interdigitated microsensor electrodes components of prototransducers were also characterized by Electrochemical Impedance Spectroscopy (EIS) over the range 1 mHz to 60 KHz using a Schlumberger Solartron 1250 Frequency Response Analyzer (FRA) interfaced through the EG&G 273 Potentiostatic to a three electrode impedance cell. The FRA-Potentiostat combination was similarly interfaced to the ACER 486PC outfitted with EG&G PAR's Model M388 data acquisition and instrument control software. Electrical conductivity measurements were made directly on the interdigitated microsensor electrodes using the small amplitude discontinuous DC pulse technique of EPSIS (EG&G PAR).

Materials 3-(1-Pyrrolyl)propionic acid was synthesized using a procedure based on a modification of Blume's [Blume, R. C.; Lindwall, H. G.; *J. Org. Chem.* 1945, 10, 255.] method. A dry, nitrogen purged flask equipped with an internal thermometer was charged with pyrrole (3.8 mL, 55.0 mmol) and benzyltrimethylammonium hydroxide (0.3 mL, 0.8 mmol, 40 wt % solution in methanol). To this solution was added acrylonitrile (2.9 mL, 55.0 mmol) without allowing the reaction temperature to rise above 40° C. After the addition was complete the reaction was stirred for 24 hours. The crude nitrile was then hydrolyzed by adding potassium hydroxide (4.0 g, 71.4 mmol) in 10 mL of water to the reaction mixture and heating to reflux for 2 hours. After allowing the reaction to cool to room temperature, the product was isolated by acidification with 6N HCl followed by extraction with ether (4×). The combined organic extracts were dried over anhydrous sodium sulfate and the solvent removed in vacuo to give a product which was purified by distillation (127° C./3 mm Hg) to afford 6.0 g (78%) of the title compound as a white solid—Mp 59°–60° (lit. 59°–60°) FT-IR (KBr) 2964 (br), 1717 (br), 1497, 1441, 1405, 1364, 1333, 1282, 1251, 1210, 1169, 1087, 1061, 923, 733, 620 cm-1. $^1$H NMR (300 MHz, CDCl$_3$) δ 6.6. (t, J=2.1 Hz, 2 H), 6.13 (t, J=2.2 Hz, 2 H), 4.19 (t, J=6.8 Hz, 2 H), 2.82 (t, J=6.8 Hz, 2 H). Pyrrole (Py) was supplied by Aldrich and was used after distillation under reduced nitrogen pressure. 3-Aminopropyltrimethoxysilane (Aldrich), N-hydroxysulfosuccinimide (sulfo-NHS) (Pierce), 1,3-diisopropylcarbodiimide (DIPC) (Chemical Dynamics) and (ααα-trifluro-p-tolyl) acetic acid (Aldrich) were purchased and used as supplied. The solvents acetone, 2-propanol, acetonitrile, and Omnisolve triply distilled water were used as supplied. Phosphate buffered potassium chloride (PBKCl), pH 7.2, was prepared in the standard way [CRC Handbook of Physics and Chemistry, CRC Press ]. Planar gold (PME-Au), planar platinum (PME-Pt) and micro Ag°/AgCl 3M Cl⁻ reference electrodes (Model RE803) were supplied by AAI-ABTECH. The saturated calomel electrodes (SCE) were supplied by Fisher. Electropolymerization of polypyrrole (PPy) was done on prototransducer devices schematically illustrated in FIG. 1.

Electroactivity and Electropolymerization 3-(1-Pyrrolyl)propionic acid

Figure 2:
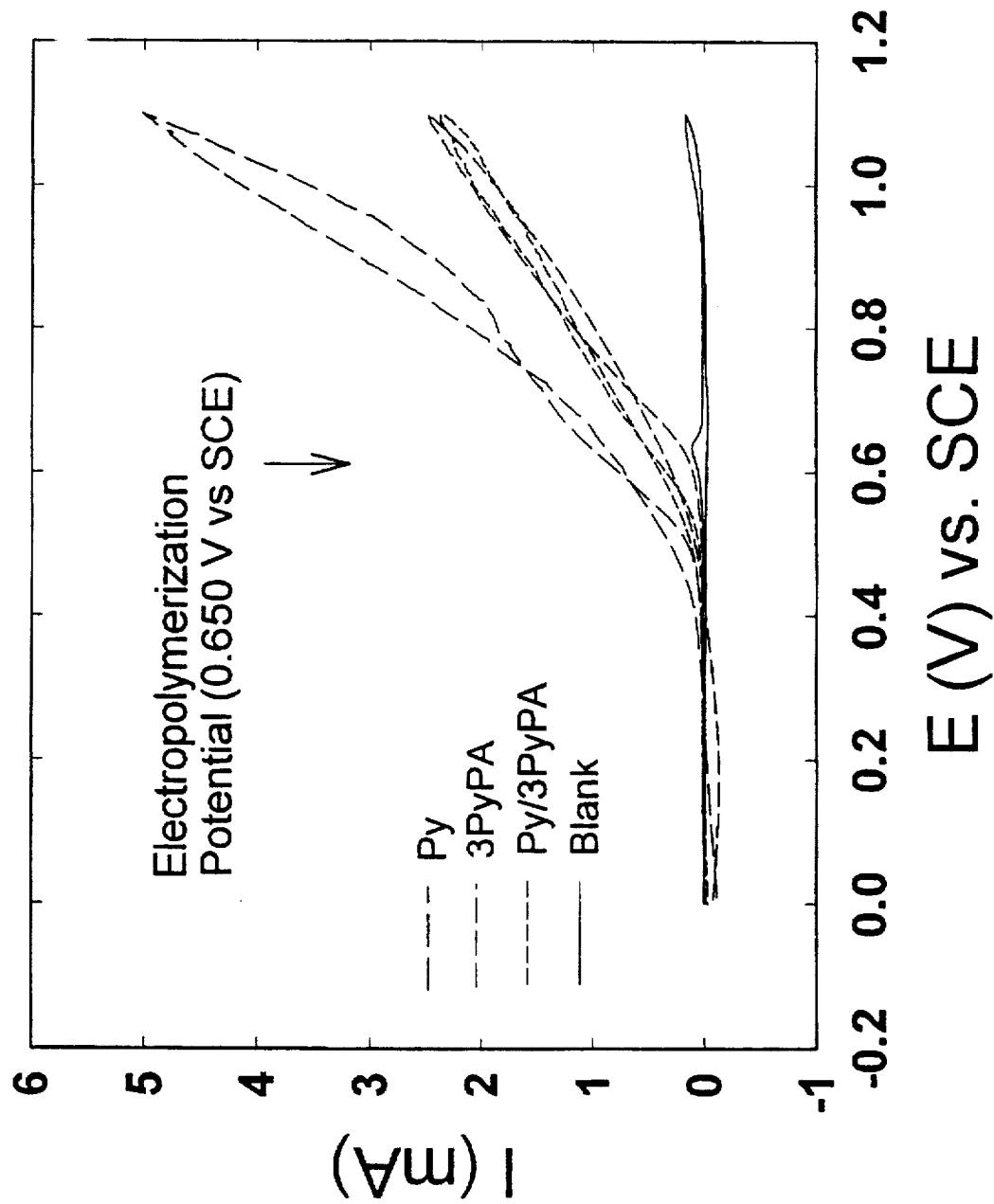
FIG. 2. Cyclic voltammograms (first scans) of pyrrole, 3-(1-pyrrolyl)propionic acid, and 50 mole % pyrrole/3-(1-pyrrolyl)propionic acid at a planar gold electrode measured over the range 0.00 to 1.00 V vs Ag°/AgCl, 3M Cl⁻ at a scan rate of 10 mV/s in 0.25 mM PSSA/0.25 mM DDBS at 20° C. and pH 2.5.

In order to effectively serve as a specific adhesion promoter, the immobilized ω-(1-pyrrolyl) moiety must be co-electropolymerized with pyrrole monomer drawn from solution and so form specific anchorage sites within the coherent and adherent polypyrrole layer on the IME device. The immobilized ω-(1-pyrrolyl) must therefore itself be electroactive and must be electropolymerizable under the conditions of electropolymerization established for pyrrole. The electroactivity of 3-(1-pyrrolyl)propionic acid was investigated to determine if it could be anodicly oxidized and so possibly participate in electropolymerization, whether on the surface or in solution. 3-(1-Pyrrolyl) propionic acid was shown to be electroactive by cyclic voltammetry at a planar gold electrode in aqueous 2.5 mM polystyrene sulfonate (PSSA)/2.5 mM dodecylbenzenesulfonate (DDBS) at pH 2.5. The supporting electrolyte of PSSA and DDBS has a pH of 3.0. The addition of 0.2M 3-(1-pyrrolyl)propionic acid reduced the pH to 2.5. FIG. 2 shows the first oxidation wave of pyrrole monomer, 3-(1-pyrrolyl)propionic acid monomer, and a 50 mole % mixture of pyrrole monomer and 3-(1-pyrrolyl)propionic acid, each compared to the blank background electrolyte. CV scans were recorded over the range 0.0 V to 1.1 V vs SCE at a scan rate of 50 mV/sec using a 1.18 cm² planar gold electrode in aqueous PSSA/DDBS solutions at 20° C. At a concentration of 0.2M, pyrrole solutions (pH=3.4), 50 mole % pyrrole and 3-(1-pyrrolyl)propionic acid solutions (pH=2.8), and the supporting electrolyte (pH=3.0) were individually pH adjusted to a pH of 2.5 by the dropwise addition of HCl.

FIG. 2 shows a single irreversible oxidation peak for all three solutions confirming the electroactivity of 3-(1-pyrrolyl)propionic acid and of the 50 mole % mixture of pyrrole and 3-(1-pyrrolyl)propionic acid. However, the oxidation wave for pyrrole commences at ca. 0.4 V and that of 3-(1-pyrrolyl)propionic acid ca 0.5 V vs Ag°/AgCl, 3M Cl⁻. This is the result of a larger overpotential for oxidation of 3-(1-pyrrolyl)propionic acid relative to pyrrole. Additionally, the pyrrole monomer shows a considerably higher oxidation current compared to 3-(1-pyrrolyl) propionic acid and to its 50 mole % mixture with pyrrole. Both these features may be due in part to the more efficient adsorption of pyrrole monomer at the gold electrode. Interestingly, the 50 mole % mixture exactly mimics the electroactivity of 3-(1-pyrrolyl)propionic acid of equivalent concentration and the anodic current density of both is approximately half that of pyrrole monomer of equivalent concentration. In any event, these observations suggests that any resulting copolymer is likely to be richer in pyrrole than in 3-(1-pyrrolyl)propionic acid [Reynolds, J. R.; Sundaresan, N. S.; Pomerantz, M.; Basak, S.; Baker, C. K. *J. Electroanal. Chem.* 1988, 250, 355–371 ].

Figure 3:
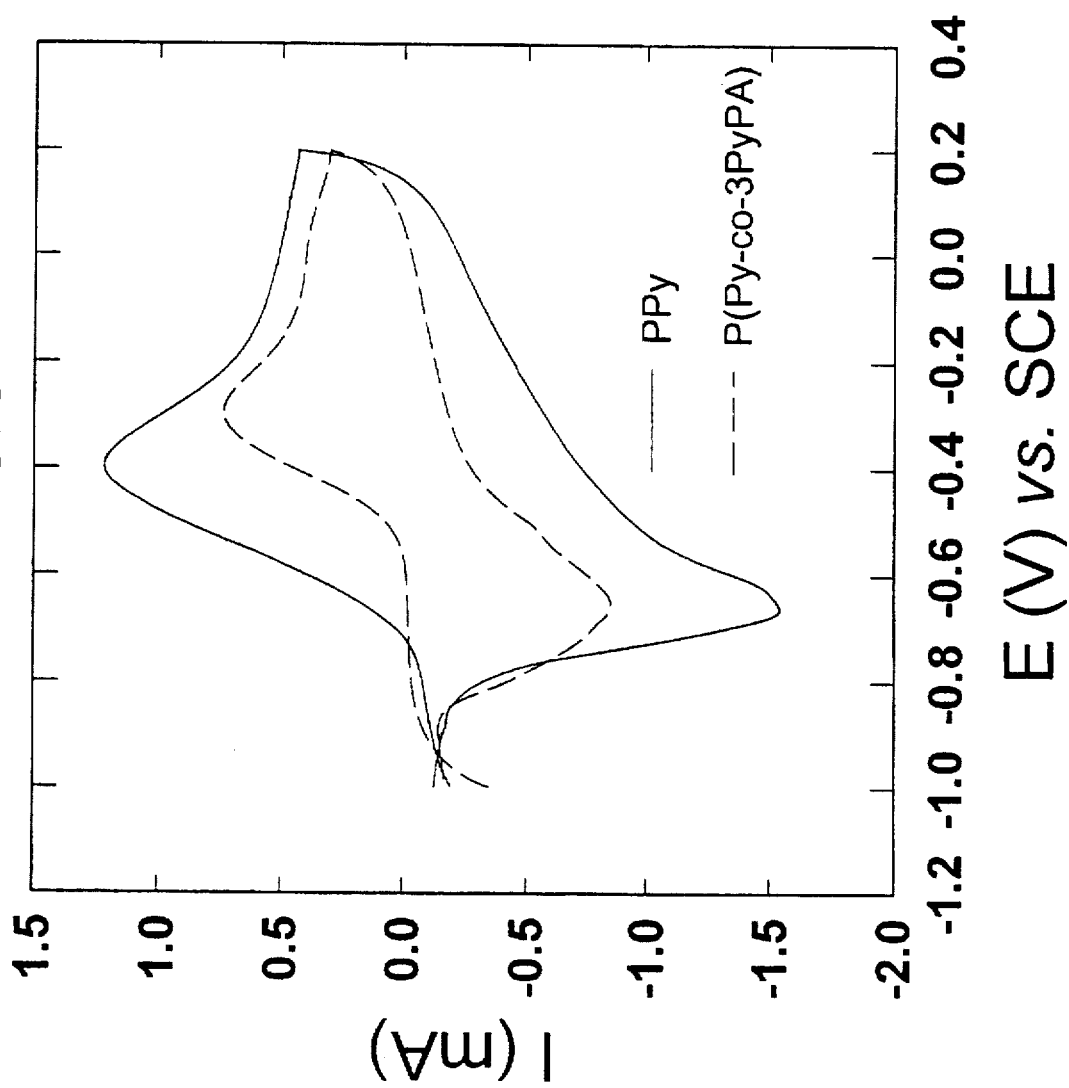
FIG. 3. Cyclic voltammograms of electropolymerized polypyrrole and electropolymerized poly(pyrrole-co-3-(1-pyrrolyl)propionic acid) films measured over the range −1.00 to 0.00 V vs Ag°/AgCl, 3M Cl⁻ at a scan rate of 10 mV/s in deaerated 0.10M KCl at 20° C.

The electropolymerizability of 3-(1-pyrrolyl)propionic acid and the 50 mole % pyrrole and 3-(1-pyrrolyl)propionic acid mixture were also investigated and compared to established electropolymerizability of pyrrole. When held at a potential of 0.65 V vs Ag°/AgCl, 3M Cl⁻, the solution of 3-(1-pyrrolyl)propionic acid and the 50 mole % pyrrole and 3-(1-pyrrolyl)propionic acid mixture, like pyrrole, each produced a coherent black polymer film at a planar gold electrode. This confirmed the ability of 3-(1-pyrrolyl) propionic acid to the electropolymerized and further suggests that it may be readily co-polymerized with pyrrole. Films of the various polymers were grown from aqueous 0.25 mM PSSA/0.25 mM DDBS solutions at 20° C. to a total electropolymerization charge, $Q_e$, of 70 mC/cm². Linear sweep cyclic voltammetry (CV) at a 10 mV/s sweep rate over the potential range −1.00 V to 0.00 V vs Ag°/AgCl, 3M Cl⁻ was performed in deaerated 0.10M KCl and was used as a standard method to characterize these electropolymerized polymer films. The integrated anodic current obtained in a single sweep over this range served to establish the anodic charge density, $Q_a$ (mC/cm²), of the film. The anodic charge density, $Q_a$, obtained in this way was used to evaluate and compare the electroactivity of the various polypyrrole films formed from the various monomer solutions. FIG. 3 shows the cyclic voltammograms of the various potentiostatically electropolymerized polypyrrole films obtained under these standard conditions. Films display the expected oxidation and reduction half waves [Reynolds, J. R.; Sundaresan, N. S.; Pomerantz, M.; Basak, S.; Baker, C. K. *J. Electroanal. Chem.* 1988, 250, 355–371.] associated with polypyrrole. Table 2 summarizes key electrochemical characteristics of these various polypyrrole films fabricated on planar gold electrodes.

Poly(3-(1-pyrrolyl)propionic acid) films of equivalent electropolymerization charge density required electropolymerization times as much as ca. 3.5 times as long compared to polypyrrole films. Under these conditions the poly(3-(1-pyrrolyl)propionic acid) films were very poorly adhered to gold or to platinum electrodes at either neutral or at low pH and they lacked the physical integrity of polypyrrole films or of the copolymer films. The poly(3-(1-pyrrolyl)propionic acid) film rapidly disbonded during attempts to obtain anodic charge density via cyclic voltammetry in 0.1M KCl at 20° C. Films formed from 50 mole % pyrrole and 3-(1-pyrrolyl)propionic acid required only slightly longer electropolymerization times but contained approximately half the charge density of polypyrrole films, had a more positive $E^{o'}$ suggesting a larger overpotential for oxidation, and displayed a larger $\Delta E_p$ suggesting a greater influence of the 3-(1-pyrrolyl)propionic acid monomer on the diffusion of potassium ions into and out of the film.

TABLE 2

Electrochemical characteristics of electropolymerized polypyrrole-based films formed on planar gold electrodes from 0.25 mM PSSA/0.25 mM DDBS at 20° C. and electroanalyzed by CV in 0.1 M KCl at 20° C. over the range −1.0 V to +0.2 V vs SCE at a scan rate of 10 mV/sec.

|  | Pyrrole | 50 mole % Pyrrole/3-(1- | 3-(1-Pyrrolyl) propionic |
|---|---|---|---|
| Electropolymerization Time (min.) | 21.42 | 23.18 | 71.57 |
| Electropolymerization Charge | 70.03 | 70.03 | 69.74 |
| CV Anodic Charge Density, $Q_a$, | 61.14 | 33.34 | — |
| $E_{pa}^{1/2}$ (mV); $i_{pa}^{1/2}$ | −394; 1.219 | −292; 0.740 | — |

TABLE 2-continued

Electrochemical characteristics of electropolymerized polypyrrole-based films formed on planar gold electrodes from 0.25 mM PSSA/0.25 mM DDBS at 20° C. and electroanalyzed by CV in 0.1 M KCl at 20° C. over the range −1.0 V to +0.2 V vs SCE at a scan rate of 10 mV/sec.

| | Pyrrole | 50 mole % Pyrrole/3-(1- | 3-(1-Pyrrolyl) propionic |
|---|---|---|---|
| (mA) | | | |
| $E_{pc}^{1/2}$ (mV); $i_{pc}^{1/2}$ | −662; −1.541 | −652; −0.853 | — |
| (mA) | | | |
| $\Delta E_p$ (mV) | 268 | 360 | — |
| $E^{o'}$ (mV) | −528 | −472 | — |

Surface Modification and Derivatization of Prototransducers

The prototransducer devices were cleaned in a Branson 1200 Ultrasonic Cleaner by sequential washing—first in acetone, followed by 2-propanol and finally in Omnisolve water. Prior to silanization, the devices were cleaned for 5 min. in a UV/ozone cleaner, UV_Clean™ (Boekel Industries, PA), to remove adventitiously adsorbed organics. The chemically cleaned prototransducer device, schematically illustrated in FIG. 4a, was then immersed for 10 min. in a freshly prepared solution of 2% 3-aminopropyltrimethoxysilane in 95% ethanol/5% water. The adsorbed and hydrogen bonded silanol layer formed on the surface was rinsed profusely with ethanol then cured at 110° C. for 10 min. before being cleaned again in a Branson 1200 Ultrasonic Cleaner by sequential washing—first in heptane, followed by acetone, then 2-propanol and finally in Omnisolve water. This yield the amino silanized surface shown in FIG. 4b that possesses free primary amine functionalities. To achieve specific adhesion of electropolymerized PPy films, the interdigit space of the IME component of the prototransducer was subsequently derivatized to produce an electropolymerizable ω-(1-pyrrolyl) derivative. The amino silanized surface modified device was derivatized by immersion into a freshly prepared aqueous solution containing N-hydroxysulfosuccinimide (Sulfo-NHS) (0.1 mg/ml), 1,3-Diisopropylcarbodiimide (DIPC) (0.1 mg/ml) and 3-(1-pyrrolyl)propionic acid (0.1 mg/ml). The device was stirred gently and allowed to incubate for 1 hr at 20° C. to derivatize the surface. The ω(1-pyrrolyl) derivatized interdigit spaces illustrated in FIG. 4c resulted from a simple two step modification and derivatization procedure in which the borosilicate glass surface was first modified via silanization with 3-aminopropyltrimethoxysilane and the primary amine of the siloxane monolayer directly linked to 3-(1-pyrrolyl) propionic acid using carbodiimide linking chemistry. To compare the effectiveness of the specific adhesion promoter, similar devices were rendered hydrophobic by modification of their interdigit spaces with the long chain n-alkane dodecyltrichlorosilane (FIG. 4d). Surface modification with dodecyltrichlorosilane was similarly performed from a 2% solution in anhydrous ethyl alcohol. To facilitate XPS analysis of the modified and derivatized surfaces and to permit determination of coverage and conversion efficiencies from XPS data, glass surfaces were also derivatized with (ααα-trifluro-p-toyl)acetic acid to yield the derivatized surface shown in FIG. 4e. Where derivatization with (ααα-trifluro-p-tolyl)acetic acid was needed, the 3-(1-pyrrolyl)propionic acid was replaced with (ααα-trifluro-p-tolyl)acetic acid of equivalent concentration. FIG. 4 therefore summarizes the various steps used in the surface modification and derivatization of the IME devices. For X-ray Photoelectron Spectroscopic (XPS) analysis, surface chemical modification, functionalization, and derivatization was performed on 1 cm×1.75 cm plates of the chemically resistant, electronics quality borosilicate glass as well as on oxidized silicon.

X-ray photoelectron spectroscopic analysis of the different chemically modified and/or derivatized surfaces prepared were studied on a Scienta ESCA300 spectrometer using a monochromatized Al Kα radiation source at 1486.6 eV. Survey scans were recorded at 300 eV pass energy with a 0.50 eV energy step. The survey scans clearly showed the presence of nitrogen containing moieties on the silanized and derivatized surfaces—a signal that was not evident on the un-silanized silicon oxide surface. There was also a significant increase in the intensity of the $C_{1s}$ peak of the silanized and derivatized surfaces compared to the un-silanized silicon oxide surface. This confirmed the successful introduction of organic moieties to the surface of the oxide. The survey scan of the surface derivatized with α,α,α-(trifluro-p-tolyl) acetic acid showed a clear $F_{1s}$ signal at ca. 688 eV. This signal was not present on the un-silanized silicon oxide surface or either of the 3-aminopropyltrimethoxysilane silanized or ω-(1-pyrrolyl) derivatized surfaces. The presence of this $F_{1s}$ signal confirmed that surface derivatization using carbodiimide linking chemistry was capable of directly linking the solution phase free acid to the immobilized 1° amine of the 3-aminopropyltrimethoxysilane silanized surface.

The intensities of the $N_{1s}$, $C_{1s}$, $O_{1s}$, $Si_{2p}$ and $F_{1s}$ peaks associated with these survey scans were also determined. For each energy region studied, the peak intensity was determined at three different take-off angles and at a pass energy of 300 eV with 0.06 eV energy steps. The take-off angles of 10° (surface sensitive), 45° (intermediate) and 90° (bulk sensitive), were used in order to obtain some information about the depth distribution of the elements in the film. Table 3 shows the peak intensities obtained at the various take-off angles used. It is apparent from the oxygen to silicon ratio that the pristine oxide surface possesses an unexpectedly large amount of oxygen and some carbonaceous material. The $C_{1s}$ signal of the bare oxide surface was centered at 284.8 eV and quite low in intensity. This $C_{1s}$ and $O_{1s}$ signal intensities both show an appreciable increase, while the $Si_{2p}$ intensity shows a corresponding decrease, as the take-off angle is lowered from 90° through 10°. This suggests the presence of surface species that were likely adventitiously adsorbed carbonaceous moieties as well as strongly adsorbed water within the near surface of the oxide.

TABLE 3

Absolute and arbitrarily normalized (to $Si_{2p}$) XPS peak intensities of the various modified and derivatized surfaces.

| Take-off Angle | Element | Unmodified Silicon | | 3-aminopropyl | | 3 (1-pyrrolyl) | | α, α, α (trifluro-p |
|---|---|---|---|---|---|---|---|---|---|
| 10° | $C_{1s}$ | 254 | 0.49 | 698 | 5.06 | 959 | 4.46 | 1683 | 4.38 |
| | $N_{1s}$ | 0 | 0 | 383 | 2.78 | 337 | 1.57 | 578 | 1.51 |
| 45° | $C_{1s}$ | 565 | 0.13 | 5286 | 4.48 | 3250 | 1.15 | 2853 | 0.96 |
| | $N_{1s}$ | 0 | 0 | 3289 | 2.79 | 1485 | 0.53 | 1343 | 0.45 |
| 90° | $C_{1s}$ | 366 | 0.09 | 4103 | 4.18 | 2140 | 0.76 | 1968 | 0.58 |
| | $N_{1s}$ | 0 | 0 | 2664 | 2.72 | 999 | 0.35 | 958 | 0.28 |

Upon surface amination, the $C_{1s}$ signal intensity increases 10-fold and the $N_{1s}$ signal, previously absent, appears as two symmetrical peaks—a major peak centered on 399.2 eV and a minor peak centered on 400.8 eV. Derivatization of the primary amine with 3-(1-pyrrolyl)propionic acid via carbodiimide linking produces a shift toward higher binding energy of the $N_{1s}$ peaks. The previously major peak now appears at 399.8 eV and the former minor peak now appears at 401.6 eV. This latter peak also displays a significant increase in signal intensity. Shown in FIG. 5, the peak at 399.8 eV is associated with the amide formed by the carbodiimide linking reaction and the latter peak is assigned to the $N_{1s}$ of the aromatic ω-pyrrolyl moiety. The presence of 2° amine nitrogen and the aromatic nitrogen is seen as clear and convincing evidence for the successful derivatization of the 1° amine of the aminosilane. Supporting evidence for the successful derivatization of the primary amine of the 3-aminopropyltrimethoxysilane silanized surface is found in the derivatization reaction with α,α,α-(trifluro-p-tolyl) acetic acid. Surface derivatization with this compound via carbodiimide linking produces a new, single symmetrical peak centered at 688.5 eV. The presence of this fluorine peak is further evidence for the direct linking of the 1° amine of the immobilized aminosilane with the solution phase acid.

Fabrication of Chemically Responsive Transducers

Chemically responsive transducers were fabricated from prototransducers by the growth or deposition of an electroconductive polymer film onto the IME component of the prototransducer. Deposition of electroconductive polymer films was achieved by electropolymerization, although spin casting of chemically synthesized polymer may also be used to yield a film or spontaneous chemical polymerization at the surface of the device may be used to achieve film growth. Typically, potentiostatic electropolymerization was used, although potentiodynamic electropolymerization, and galvanostatic electropolymerization may also be used.

Having established the electroactivity and electropolymerizability of 3-(1-pyrrolyl)propionic acid, and the co-electropolymerizability of 3-(1-pyrrolyl)propionic acid with pyrrole it was possible to approach with confidence the electropolymerization of polypyrrole films onto surface modified prototransducer devices. Potentiostatic electropolymerization of polypyrrole films at the surface of unmodified, modified, and modified and derivatized IME components was carried out by applying a potential of +0.65 V vs Ag°/AgCl, 3M Cl⁻ to the combined/shorted electrodes of the IME component of the prototransducer. The film grew on each electrode and also between the digits of the pair of electrodes. The electropolymerization bath was typically prepared to contain 0.20M pyrrole, 2.5 mM poly (styrenesulfonic acid), 2.5 mM dodecylbenzenesulfonate (sodium salt) and 1 mg/ml poly(1-lysine) at a pH of 3.0, although other bath compositions are possible as shown in the cited examples, and maintained at a constant temperature of 20° C. in an EG&G PAR Model K2064 water-jacketed micro-electrochemical cell. The constant temperature was produced using a Lauda K-2/R refrigerated constant temperature circulator. Films were electropolymerized to a total anodic electropolymerization charge density, $Q_e$, of $2.9 \times 10^{-3}$ C/cm².

The time required to discharge each PPy film is a measure of the electropolymerization kinetics of polymer film growth on that device. The chemical surface modification of the interdigit space of the device had only a modest influence on the electropolymerization kinetics. PPy films grown on unmodified glass surfaces required the longest electropolymerization time of ca. 23 min. Films grown on aminopropyltrimethoxysilane-modified surfaces required the shortest electropolymerization time of ca 16 min. The electropolymerization time for the polypyrrole films grown on the various surfaces was observed to occur in the order; unmodified surface (23.17 min.)>>dodecyltrichlorosilane-modified surface (17.98 min.)>ω-(1-pyrrolyl) derivatized surface (17.17 min.)>3-aminotrimethoxysilane-modified surface (16.10 min.). It is arguable that there is essentially no difference in the polymerization kinetics arising from the various substrate surface chemistries. Films were electropolymerized such that they completely bridged the interdigit space and formed a fully contiguous layer over the active device surface. In this way electrochemical, electrical, and adhesion measurements could be made on the film. At the end of each electropolymerization, the devices were removed, rinsed thoroughly in 0.1M KCl and characterized by cyclic voltammetry (CV), EPSIS conductivity testing, and adhesion testing.

Figure 6:
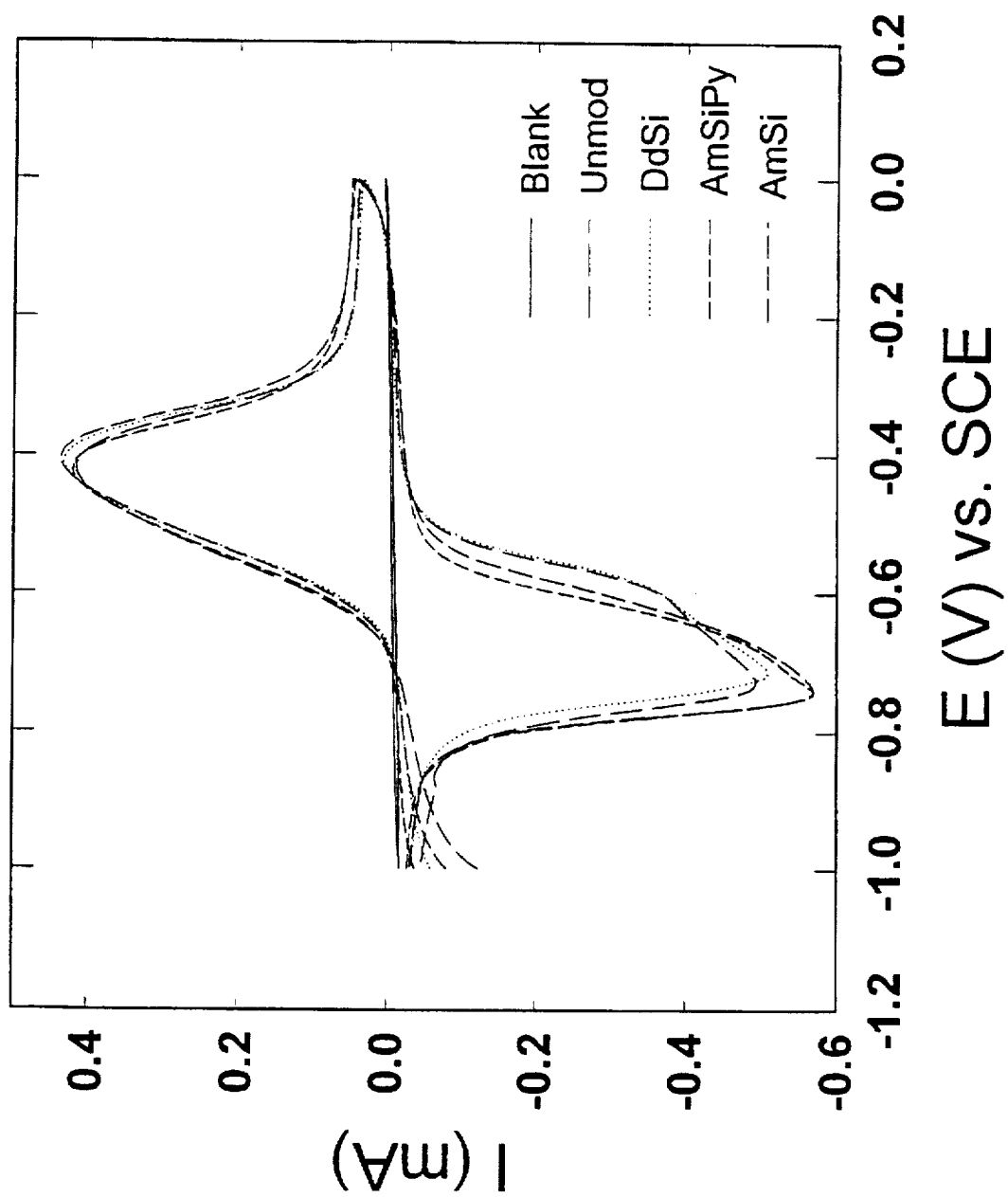
FIG. 6. Cyclic voltammograms of electropolymerized polypyrrole films grown on surface modified and or derivatized IME devices and measured over the range −1.00 to 0.00 V vs Ag°/AgCl, 3M Cl⁻ at a scan rate of 10 mV/s in deaerated 0.10M KCl at 20° C.

CV Characterization: Linear sweep cyclic voltammetry (CV) at a 10 mV/s sweep rate over the potential range −1.00 to 0.00 V vs Ag°/AgCl, 3M Cl⁻ in dearated 0.10M KCl held at 20° C. was used as a standard method to charactized the electropolymerized polypyrrole films. The integrated anodic current obtained in a single sweep over this range served to establish the anodic charge density, $Q_a$ (mC/cm²), of the film. The anodic charge density, $Q_a$, obtained in this way was used to evaluate and compare the electroactivity of the PPy films formed on the various interdigitated microsensor array electrodes. FIG. 6 shows cyclic voltammograms of potentiostatically electropolymerized polypyrrole films grown over these chemically modified surfaces and obtained under these standard conditions. Films display the expected oxidation and reduction half waves [Reynolds, J. R.; Sundaresan, N. S.; Pomerantz, M.; Basak, S.; Baker, C. K. J. Electroanal. Chem. 1988, 250, 355-371.] typical of polypyrrole with $E_{pa}^{1/2}$ centered around −0.42 V and $E_{pc}^{1/2}$ centered around −0.73 V vs Ag°/AgCl, 3M Cl⁻. Films grown on unmodified surfaces and on dodecyltrichlorosilane-modified surfaces do however display a small shoulder in the cathodic half wave around 0.6 V vs Ag°/AgCl, 3M Cl⁻. Table 4 summarizes important electrochemical characteristics of the polypyrrole films grown on these various chemically modified surfaces.

TABLE 4

Electrochemical and electrical properties of electropolymerized polypyrrole films
formed on various surface modified interdigitated microsensor electrode portion of
sensor devices and electroanalyzed by cyclic voltammetry in 0.1 M KCl at 20° C.
over the range −1.00 V to +0.00 V vs Ag°/AgCl, 3 M Cl⁻ at a scan rate of 10 mV/sec.

| | Surface Chemical Modification of the IME Interdigit Space | | | |
|---|---|---|---|---|
| | Unmodified | Dodecyltri-chlorosilane | 3-Amino-propyltri-methoxysilane, 3-(1-pyrrolyl) propionic acid | 3-Amino-propyltri-methoxysilane |
| Electropolymerization Time (min.) | 23.17 | 17.98 | 17.17 | 16.10 |
| Electropolymerization Charge Density, $Q_e$, (mC/cm$^2$) | 69.98 | 70.01 | 69.97 | 69.94 |
| CV Anodic Charge Density, $Q_a$, (mC/cm$^2$) | 21.13 | 20.48 | 21.30 | 21.96 |
| $E_{pa}^{1/2}$ (mV); $i_{pa}^{1/2}$ (mA) | −416; +0.415 | −410; +0.432 | −422; +0.421 | −408; +0.437 |
| $E_{pc}^{1/2}$ (mV); $i_{pc}^{1/2}$ (mA) | −725; −0.494 | −712; −0.509 | −740; −0.570 | −738; −0.569 |
| $\Delta E_p$ (mV) | 309 | 302 | 318 | 330 |
| $E^{o'}$ | −571 | −561 | −581 | −573 |
| Conductivity ($\Omega^{-1}$ cm$^{-1}$) | | | | |

Figure 7:
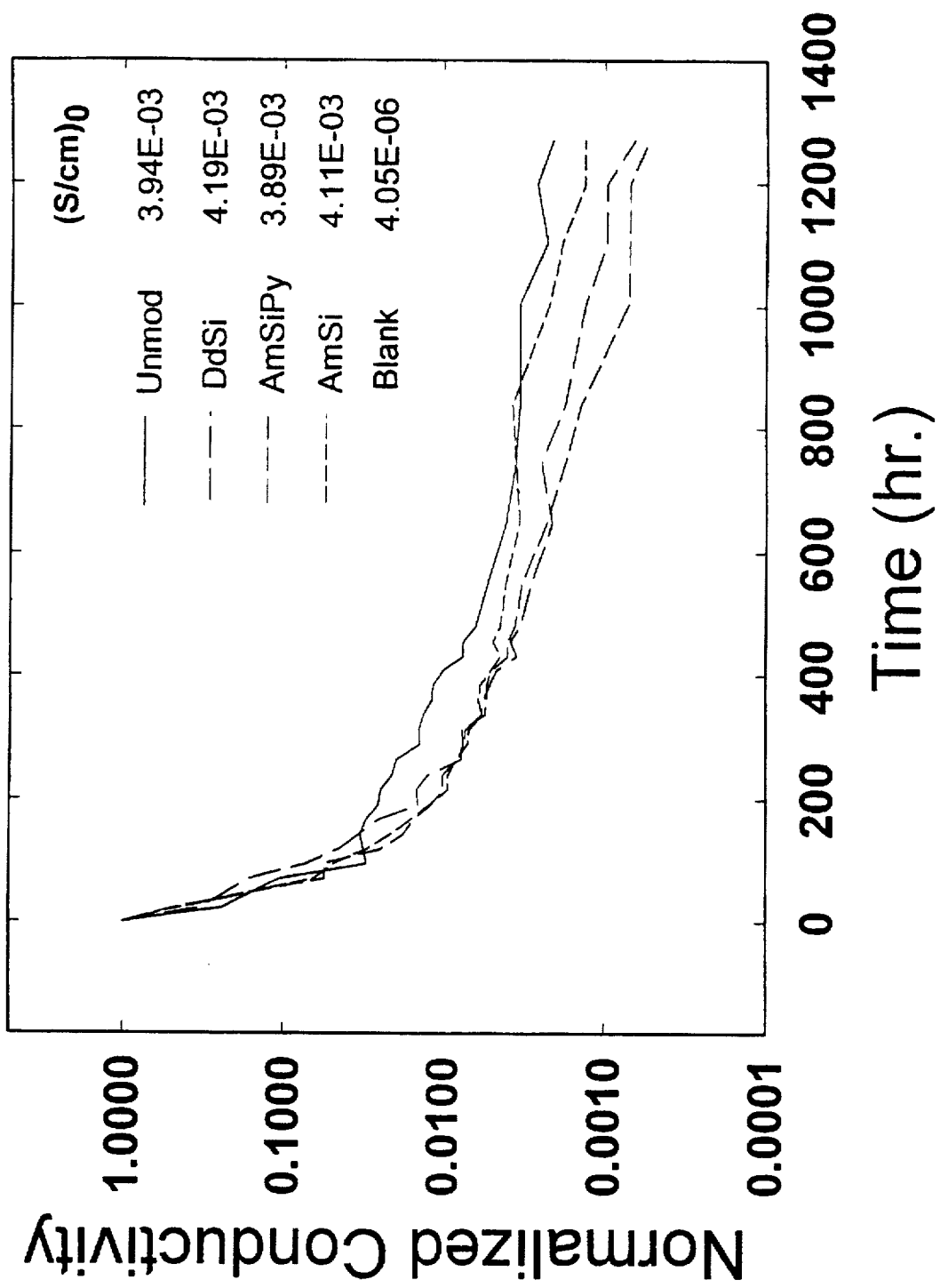
FIG. 7. Normalized electrical conductivity of electropolymerized polypyrrole thin films grown on surface modified and or derivatized IME devices and measured as a function of time of immersion in PBS 7.2 buffer at room temperature.

The anodic charge density, $Q_a$, of the polypyrrole films appears unaffected by the nature of the surface chemistry of the interdigit space over which the film is grown. Polypyrrole films grown on the various chemically modified surfaces all display a $Q_a$ value of ca. 21 mC/cm2 with a conversion efficiency in each case of ca 30%. However, the electrochemical characteristics of polypyrrole films grown on these various chemically modified surfaces fall into two distinct categories—The unmodified and purely hydrophobic dodecyltrichlorosilane-modified surface and the polar ω-amine surface of the 3-aminopropyltrimethoxysilane-modified and-3-(1-pyrrolyl)propionicacidderivatized surfaces. In addition to the shoulder at 0.6 V vs Ag°/AgCl, 3M Cl⁻ on the cathodic half wave of the polypyrrole films grown on unmodified and purely hydrophobic dodecyltrichlorosilane-modified surfaces, these films also display smaller $\Delta E_p$ values. The most striking difference occurs between the purely hydrophobic dodecyltrichlorosilane-modified surface and the hydrophilic ω-amine surface of the 3-aminopropyltrimethoxysilane-modified surface. The dodecyltrichlorosilane-modified surface has a $\Delta E_p$=0.302 V which is smallest of all the surfaces examined. By contrast the ω-amine surface of the 3-aminopropyltrimethoxysilane-modified devices has a $\Delta E_p$=0.330 V which is largest of all the surfaces examined. EPSIS™ Conductivity Testing: The electrical conductivity of freshly electropolymerized PPy films were measured in aqueous PBKCl 7.2 buffer using the small amplitude (10 mV) discontinuous DC pulse (50 ms pulse, 100 duty cycle) method of EPSIS™. EPSIS uses a non-perturbating interrogation method of small amplitude (10 mV), discontinuous, DC pulses superimposed on the open circuit potential of the electroconductive polymer film [U.S. Pat. No. 5,312,762 "Method of Measuring an Analyte by Measuring Electrical Resistance of a Polymer Film Reacting with the Analyte"]. This yields the electrical conductivity as a function of time following electrolysis at a particular potential or redox composition. The present films were electrolyzed for 3 min. at potentials corresponding to the $E^{o'}$ measured by CV analysis prior to interrogation and were interrogated for 10 cycles or 5.5 sec. The electrical conductivity was measured within 1 ms following electrolysis at the $E^{o'}$. PPy films fabricated on ω-(1-pyrrolyl) derivatized and on 3-aminotrimethoxy silane functionalized device surfaces demonstrated a higher initial electrical conductivity compared to those films fabricated on the reference surfaces. Purely hydrophobic devices functionalized with dodecyltrichlorosilane and unmodified devices showed similar but lower electrical conductivities. FIG. 7 displays the normalized conductivity of the polypyrrole films fabricated on the various chemically modified and/or derivatized device surfaces. The conductivity of the polypyrrole film on each surface can be seen to fall sharply over the first 100 hours (ca. 4 days) and then subsequently to fall more slowly up to 1400 hours (ca 58 days). The film fabricated on the unmodified device surface displays a consistently higher electrical conductivity during the second phase of conductivity decline. This is believed to result from the hydrolytic instability of the polymer/device interface that leads to buffer entering beneath the film. The presence of ions beneath the polymer presents as an apparent higher electrical conductivity.

Adhesion Testing: The adhesion of electropolymerized polypyrrole films grown on the interdigitated microsensor electrode component of prototransducer devices was performed using the familiar Scotch® tape test. The test was performed by rubbing on a strip of Scotcht® tape over the area of the device and with a smooth and continuous motion lifting the tape off beginning from one end. The adhesion of polypyrrole films to the various device surfaces was tested in this way under both wet and dry conditions. Adhesion tests on each of the four types of surfaces studied were performed in lots containing triplicate samples for each of the two test environments. Duplicate lots were performed leading to a total of 48 samples tested.

Wet Adhesion Measurements: Following electropolymerization films were rinsed in Omnisolve water and transferred to 0.1M PBKCl 7.2 buffer and maintained under immersion at room temperature. Triplicate Scotch® tape tests of each surface variation were performed at time zero and repeated after 24 hour intervals for the first 5 days and bi-weekly thereafter until adhesive or cohesive failure occurred in all three samples. Prior to performing the test, samples were sapped dry using lint free paper towels. The time to adhesive failure occurred in the order unmodified<dodecyltrichlorosilane modified<<3-aminotrimethoxysilane modified<<ω-(1-pyrrolyl) derivatized. The failure times for films immersed in aqueous PBKCl pH 7.2 buffer were 3 days<5 days<<27 days<<235 days +.

Dry Adhesion Measurements: Following electropolymerization films were rinsed in Omnisolve water and transferred to a vacuum desiccator and stored over indicating molecular sieves at room temperature. Triplicate Scotch® tape tests of each surface variation were performed at time zero and repeated after 24 hour intervals for the first 5 days and bi-weekly thereafter until adhesive or cohesive failure occurred in all three samples. The time to adhesive failure occurred in the order unmodified<dodecyltrichlorosilane modified<<3-aminotrimethoxysilane modified<<ω-(1-pyrrolyl) derivatized. The failure times under dry evacuated conditions were 3 days<30 days<<235 days+<<235 days +

EXAMPLE 1

Hydrogen Peroxide Sensor

Transducer Fabrication: Prototransducers were fabricated as previously described. Hydrogen peroxide sensitive chemical sensors were fabricated from prototransducers by the growth and deposition of an electroconductive polymer layer possessing an inorganic catalyst that rendered the transducer sensitive to $H_2O_2$. Membrane films were grown by potentiostatic electropolymerization onto the interdigit areas of chemically modified and derivatized prototransducers. The film grew on each electrode and also between the digits of the pair of electrodes such that it formed an adherent and fully contiguous membrane on the device. The film was grown from two different electropolymerization baths to form a two-layer laminate membrane. The first was a highly conducting layer that was specifically attached via surface copolymerization with immobilized ω-pyrrolyl moieties. The second was a catalyst carrying layer that was directly polymerized on the first and covalently linked to it. The first electropolymerization bath contained 0.2M pyrrole (Py), 2.5 mM poly(styrenesulfonic acid) (PSSA), and 2.5 mM sodium dodecylbenzenesulfonate (DBS) at a pH of 3.0 and at a constant T=20° C. Films were grown to a total anodic electropolymerization charge density, $Q_e$, of $6.01 \times 10^{-2}$ C/cm². The subsequent catalytic polymer layer was similarly prepared to a total anodic electropolymerization charge density, get of $2.00 \times 10^{-2}$ C/cm² from an electropolymerization bath that was neutralized by the dropwise addition of 0.015% polyvinylamine (PVAm) and also contained 1 mg/ml poly(1-lysine) and 0.1 mM $Mo_7O_{24}^{6-}$ ($Mo^{VI}$).

Figure 8B:
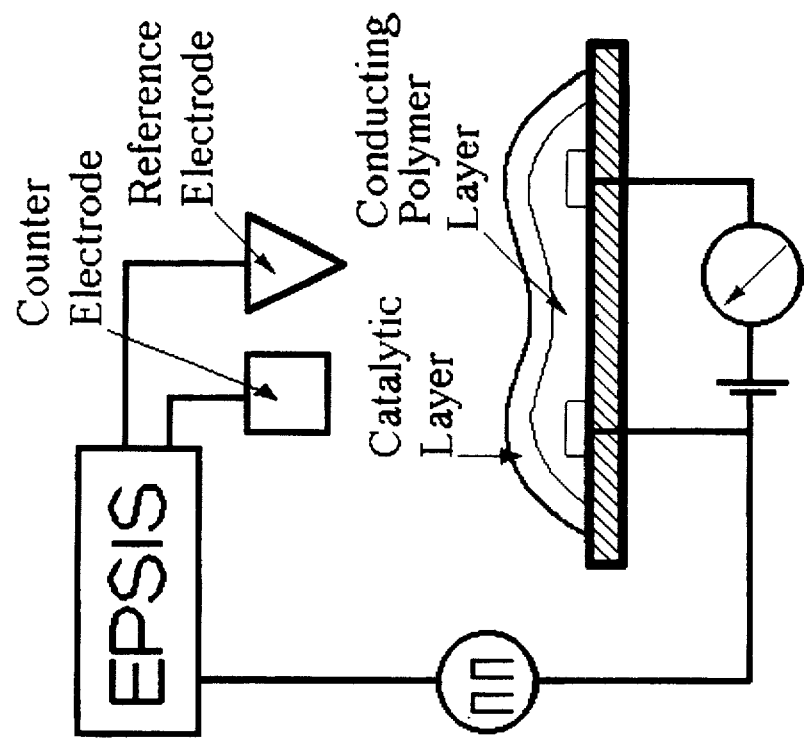
FIGS. 8A and 8B. Schematic illustration of $H_2O_2$ sensor A) showing chemistry of sensor response reactions and B) showing device structure and instrumentation.

Sensor Testing was performed using EPSIS in response to varying concentrations of $H_2O_2$ in an aqueous background of 0.5M PBKCl pH 7.2 buffer containing 1.0 mM KI. The assembled sensor instrumentation is illustrated in FIG. 8b and comprises the electroconductive polymer component of the sensor, the platinized platinum counter electrode, and the Ag°/AgCl reference electrode all connected to the EPSIS instrument hardware and software. The sensor interrogation conditions used by EPSIS were as follows: Initialization Potential: −1.000 mV; Initialization Period: 3 min.; Pulse Voltage: 10 mV; Pulse Duration: 50 ms; Delay Time: 500 ms; No. of Cycles: 327 (ca. 180 sec). In these sensor response measurements, $H_2O_2$ sensors were first electrolyzed away from their poise potential during initialization and then subsequently immediately interrogated for a total of 327 cycles or ca. 180 sec. The measured dynamically changing conductance multiplied by the cell constant of the device yields the sensor conductivity response profile.

Figure 8A:
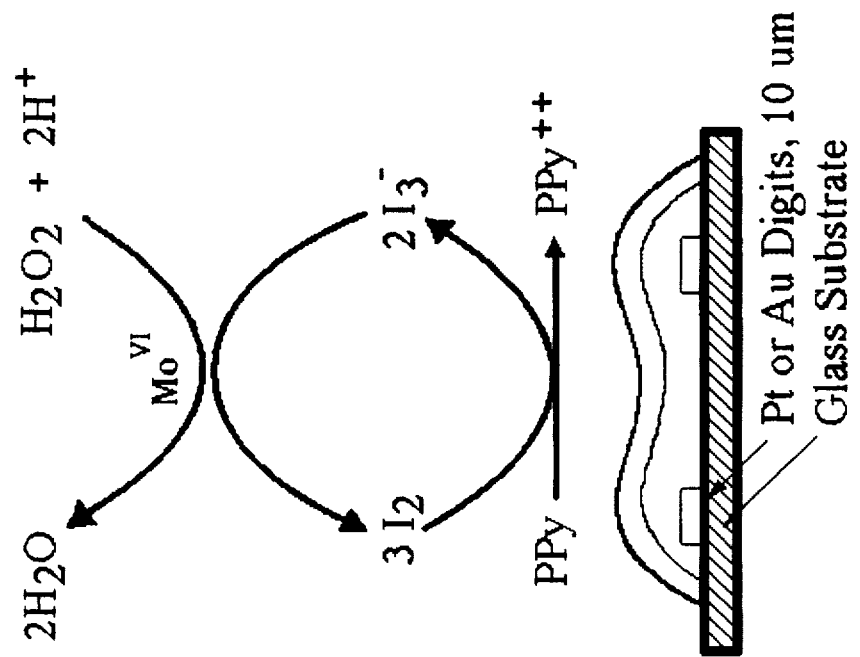

These polypyrrole-based sensors show a clear response to aqueous hydrogen peroxide in the concentration range $1 \times 10^{-6}$M to $1 \times 10^{-2}$M in PBS 7.2 buffer at room temperature. At very high concentrations of $H_2O_2$, ca $1 \times 10^{-2}$M, there is real time evidence for a degradative process occurring between the $H_2O_2$ and the electroconductive polymer film. The EPSIS conductimetric response of the device rapidly rises (as the film is oxidized) but falls as the electrical conductivity of the polymer is somehow compromised over the time course (ca. 5 min.) of an EPSIS sensor interrogation experiment. It is believed that direct oxidation by $H_2O_2$ of the highly π-conjugated polymer backbone of the PPy polymer leads to loss of carrier mobility and hence loss of electroconductive response sensitivity. This effect is greatly minimized by the formulation containing $Mo_7O_{24}^{6-}$ ($Mo^{VI}$) catalyst in the presence of iodide ion. To obviate the direct reaction of $H_2O_2$ with the PPy-based polymer transducer and hence its degradation of sensitivity, a reaction scheme was developed in which $H_2O_2$ was made to first oxidize iodide ions (I⁻) to molecular iodine ($I_2$) in the presence of catalytic amounts of $Mo^{VI}$. The iodine was then allowed to react with the PPy-based polymer transducer. Iodine is a much less aggressive oxidant compared to $H_2O_2$ and so does not contribute to oxidative degradation of the transducer membrane materials. FIG. 8a is a schematic illustration of chemistry of the $H_2O_2$ sensitive electroconductive polypyrrole-based sensor.

Prolonged immersion in aqueous media often leads to delamination of PPy films from the surface of Pt or Au IME devices. Likewise, repeated redox cycling leads to built up stresses in the film that promotes and/or accelerates delamination. Surface functionalization and derivatization greatly improves the hydrolytic stability of the PPy/substrate interface. Transducers prepared on ω-pyrrolyl modified surface have remained immersed in buffer for up to 33 weeks without delamination.

Figure 9:
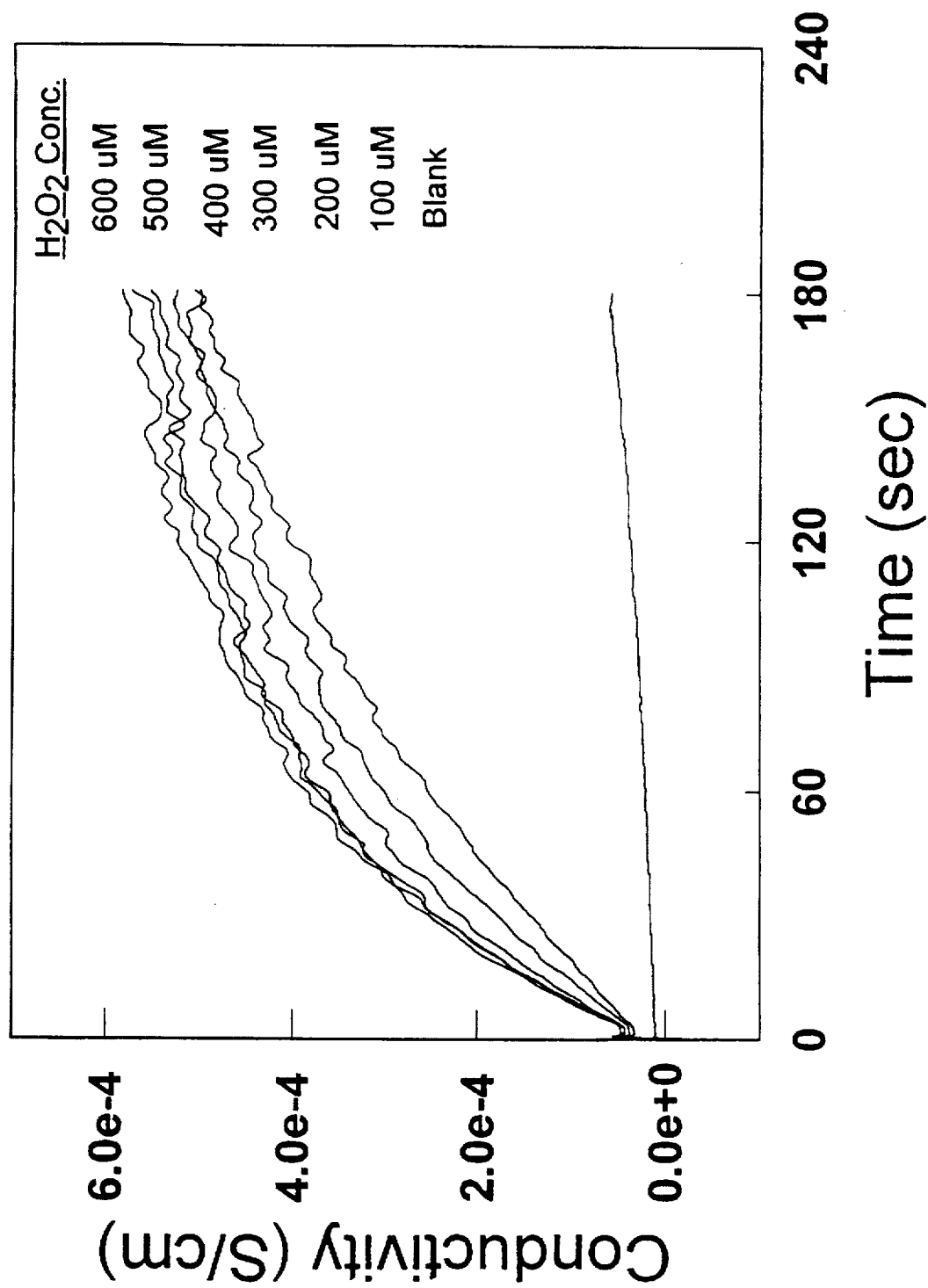
FIG. 9. Graph of the sensor response profile of various concentrations of $H_2O_2$.
Figure 10:
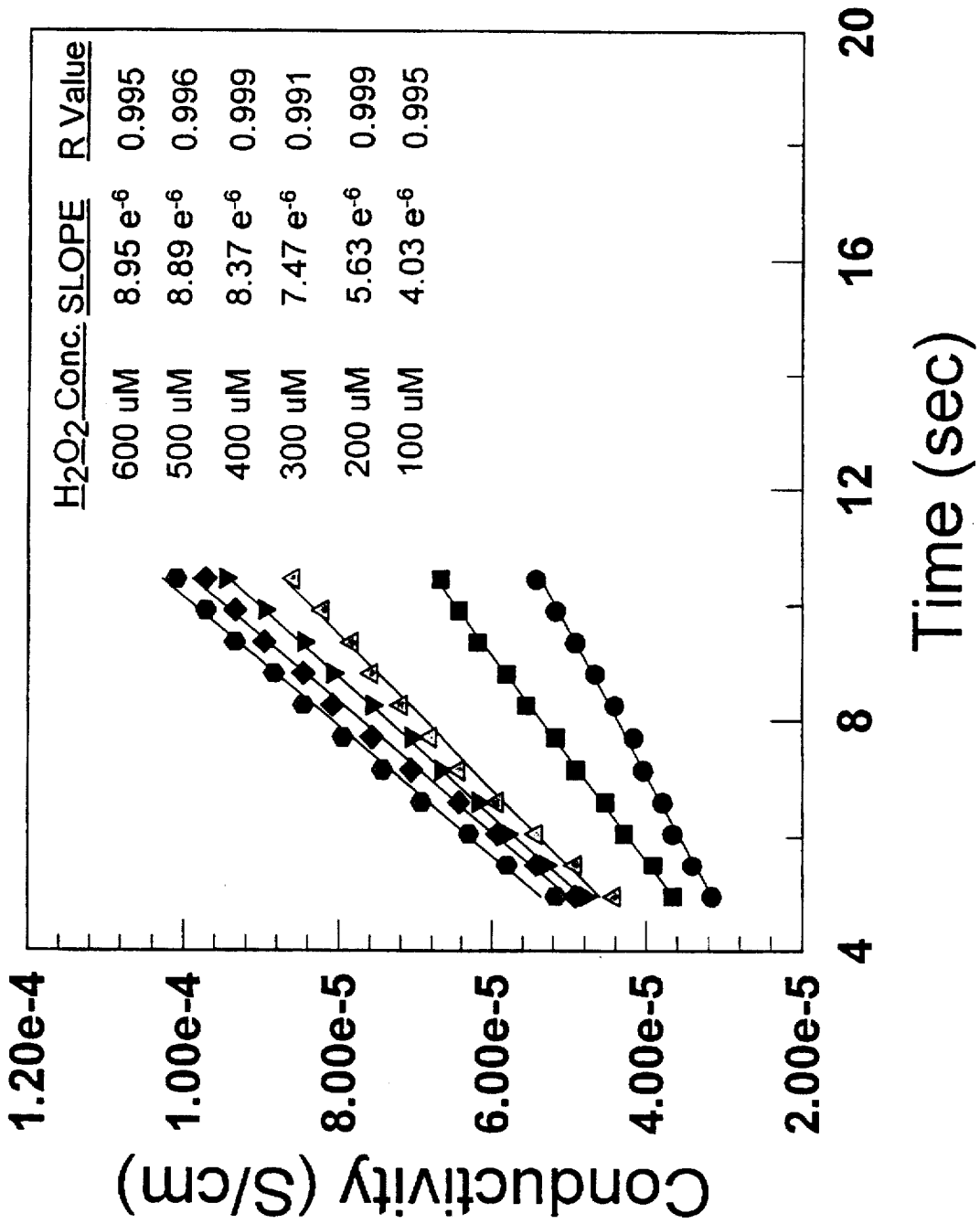
FIG. 10. Graph of the initial rate of response of various concentrations of $H_2O_2$.
Figure 11:
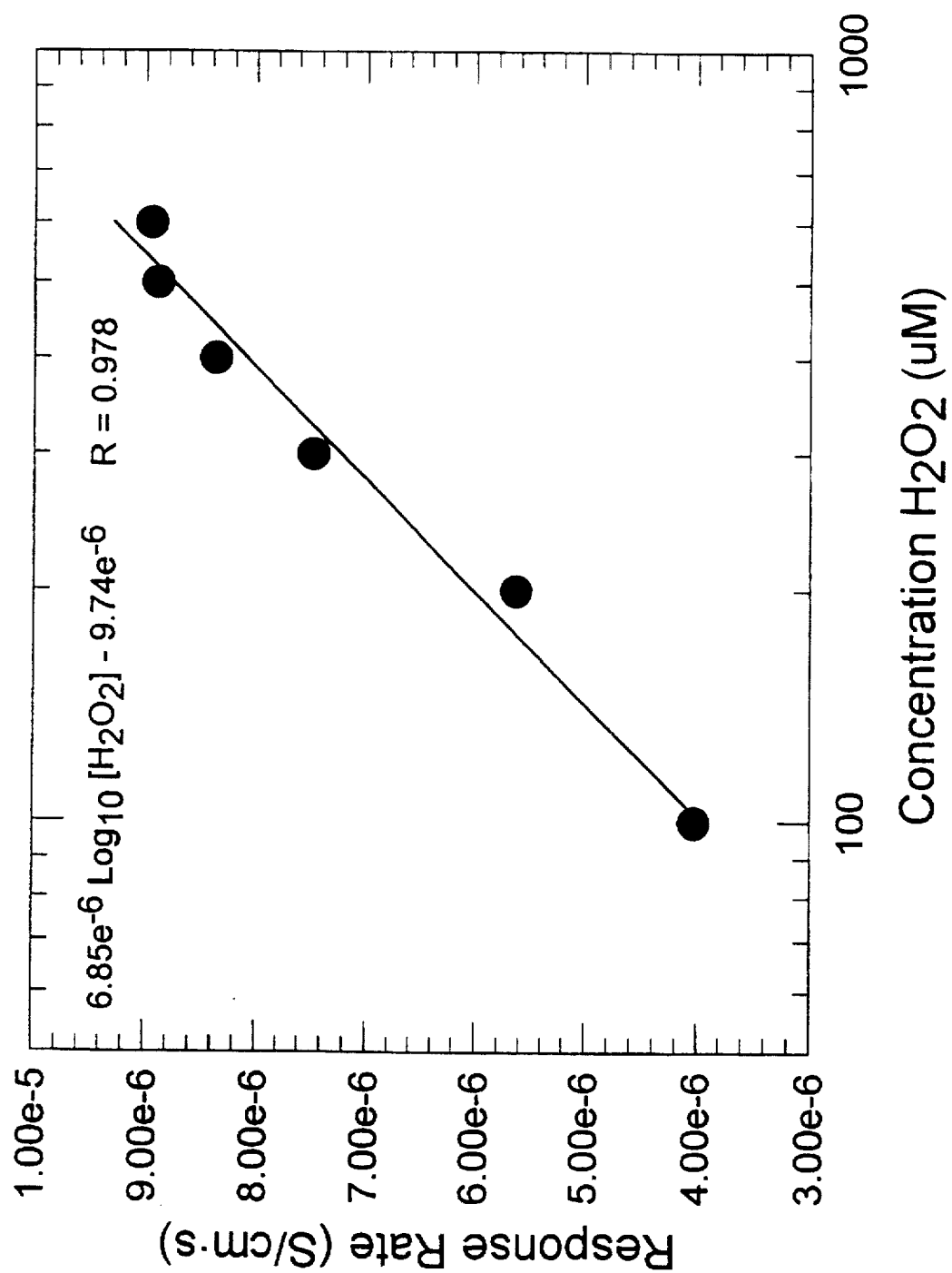
FIG. 11. Calibration of the conductimetric, $H_2O_2$-sensitive electroconductive polymer (PPy|PPy/$Mo^{VI}$) transducer at 20° C.

FIG. 9 shows the transducer's conductimetric response to varying concentrations of $H_2O_2$ in a background of 0.05M PBKCl at pH=7.2 and 1.0 mM KI at 20° C. The individual response curves rise rapidly following INITIALIZATION and reveal time dependent changes in electrical conductivity during INTERROGATION using the discontinuous, small-amplitude voltage pulses of EPSIS. The slope of the response curve at $t_0$ gives the initial rate, a kinetic response parameter, determined by the activity of $H_2O_2$. The initial responses obtained over the first 11 seconds at each concentration of $H_2O_2$ is shown in FIG. 10. Here the response of the blank is subtracted from each response curve at a given concentration to yield the initial rate curve. Also shown in FIG. 10 are the slopes (initial rates) and the corresponding correlation coefficients for each line. A plot of the initial rate parameter or slope versus concentration of $H_2O_2$ gives the calibration curve shown in FIG. 11. These results suggest a sensitivity that corresponds to almost a decade of conductivity change per decade of concentration. The availability of a general purpose $H_2O_2$-sensitive, conductimetric transducer makes it possible to develop a wide range of oxidoreductase enzyme biosensors.

EXAMPLE 2

Glucose Biosensor

Transducer Fabrication: Transducers were fabricated as previously described. Glucose sensitive chemical sensors were fabricated from transducers by the growth and deposition of an electroconductive polymer layer possessing an inorganic catalyst that rendered the transducer sensitive to $H_2O_2$ and a biospecifc layer that rendered the sensor specific to glucose. Other oxidoreductase enzymes may also be used as illustrated in the following reaction schemes:

Glucose oxidase

β-D-Glucose+$O_2$+$H_2O$→D-Gluconic acid⁻+$H_2O_2$

D-amino acid oxidase

D-amino acid+$O_2$+$H_2O$→2-keto acid⁻+$H_2O_2$+$NH4^+$

Lactate oxidase

Lactate+$O_2$→Pyruvate+$H_2O_2$

The $H_2O_2$ produced in the enzyme reaction reacts with the underlying $H_2O_2$ sensitive sensor to produce a conductimetric response that is determined by the concentration of glucose. Membrane films were grown by potentiostatic electropolymerization onto the interdigit areas of chemically modified and derivatized prototransducers. The film grew on each electrode and also between the digits of the pair of electrodes such that it formed an adherent and fully contiguous membrane on the device. The film was grown from three different electropolymerization baths to form a three layer laminate membrane. The first was a highly conducting layer that was specifically attached via surface copolymerization with immobilized ω-pyrrolyl moieties. The second was a catalyst carrying layer that was directly polymerized onto the first and covalently linked to it. The third was a biospecific layer possessing the enzyme glucose oxidase that was directly polymerized onto the second and covalently linked to it. The first electropolymerization bath contained 0.2M pyrrole (Py), 2.5 mM poly(styrenesulfonic acid) (PSSA), and 2.5 mM sodium dodecylbenzenesulfonate (DBS) at a pH of 3.0 and at a constant T=20° C. Films were grown to a total anodic electropolymerization charge density, $Q_e$, of $2.5 \times 10^{-2}$ $C/cm^2$. The subsequent catalytic polymer layer was similarly prepared to a total anodic electropolymerization charge density, $Q_e$, of $1.00 \times 10^{-2}$ $C/cm^2$ from an electropolymerization bath that was neutralized by the dropwise addition of 0.015% polyvinylamine (PVAm) and also contained 1 mg/ml poly(1-lysine) and 0.1 mM $Mo_7O_{24}^{-6}$ ($Mo^{VI}$). The third layer was similarly prepared to a total anodic electropolymerization charge density, $Q_e$, of $1.00 \times 10^{-2}$ $C/cm^2$ from an electropolymerization bath that was neutralized by the dropwise addition of 0.015% polyvinylamine (PVAm) and also contained 1 mg/ml of glucose oxidase that was conjugated via the 1° amines of lysine amino acids to 1-(3-pyrrolyl)propionic acid using carbodiimide linking chemistry.

Figures 12A, 12B:
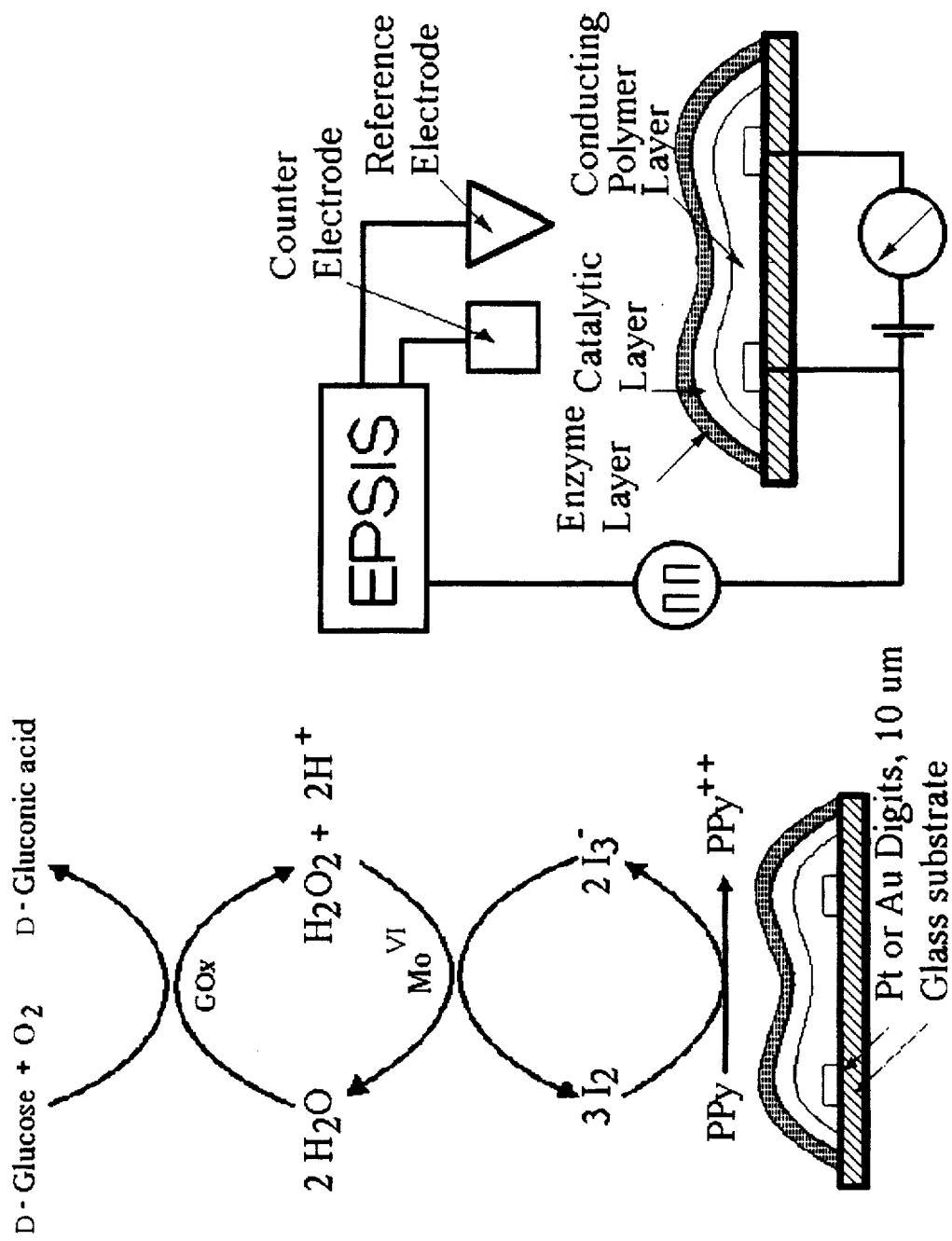
FIGS. 12A and 12B. Schematic illustration of glucose biosensor A) showing chemistry of sensor response reactions and B) showing device structure and instrumentation.

Sensor Testing was performed using EPSIS in response to varying concentrations of glucose in an aqueous background of 0.5M PBKCl pH 7.2 buffer containing 1.0 mM KI. FIG. 12a is a schematic illustration of the glucose sensitive electroconductive polypyrrole-based transducer. The assembled transducer is illustrated in FIG. 12b and comprises the electroconductive polymer component of the sensor, the platinized platinum counter electrode, and the Ag°/AgCl reference electrode each connected to the EPSIS instrument hardware and software. The sensor interrogation conditions used by EPSIS were as follows: Initialization Potential: −800 mV; Initialization Period: 3 min.; Pulse Voltage: 15 mV; Pulse Duration: 50 ms; Delay Time: 500 ms; No. of Cycles: 327 (ca. 180 sec). In these sensor response measurements, glucose sensors were first electrolyzed away from their poise potential during initialization and then subsequently immediately interrogated for a total of 327 cycles or ca. 180 sec. The measured dynamically changing conductance multiplied by the cell constant of the device yields the sensor response profile.

Figure 13:
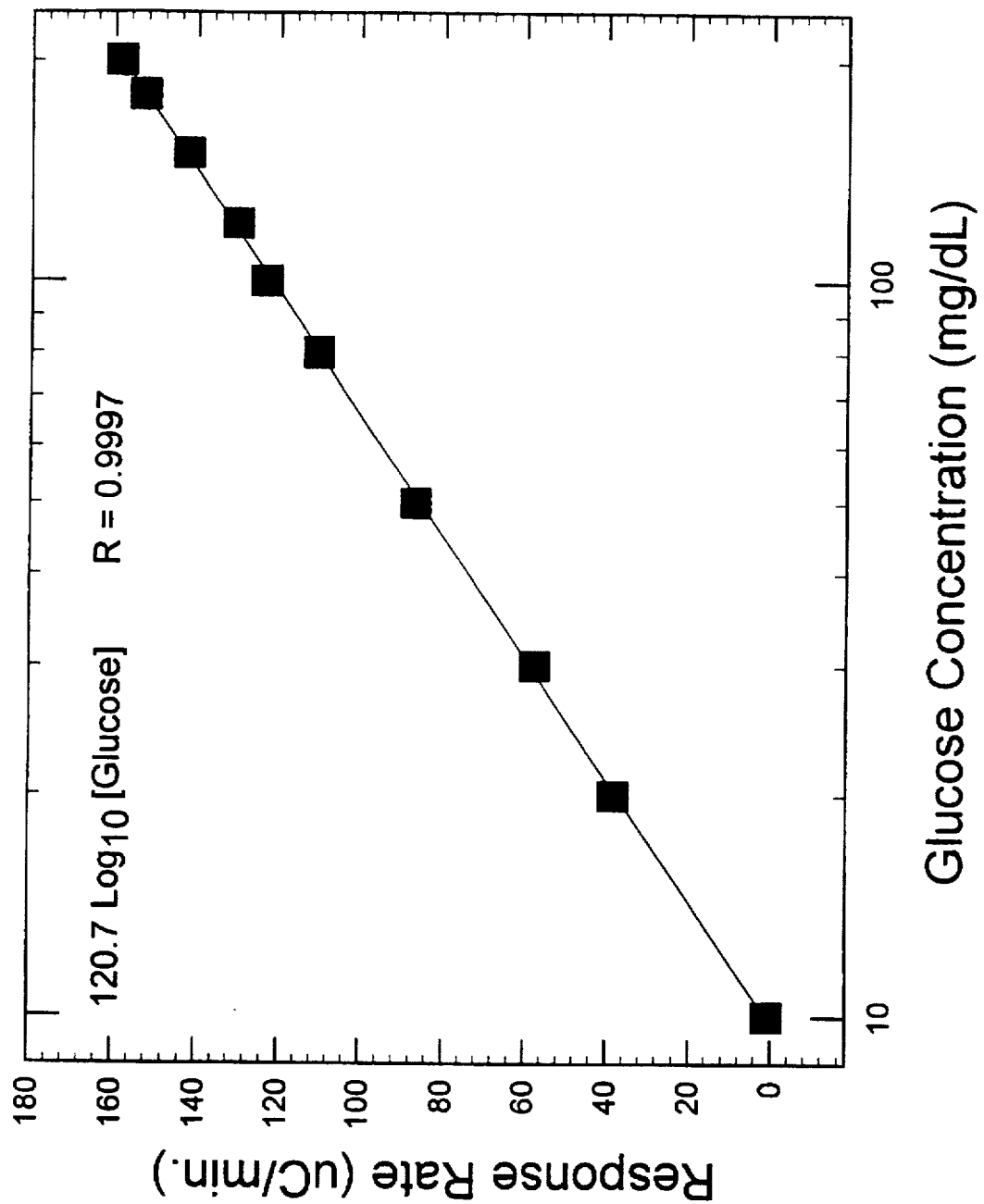
FIG. 13. Calibration of the conductimetric, glucose-sensitive electroconductive polymer (PPy|PPy/$Mo^{VI}$|PPy/Gox) enzyme biosensor.
Figure 14B:
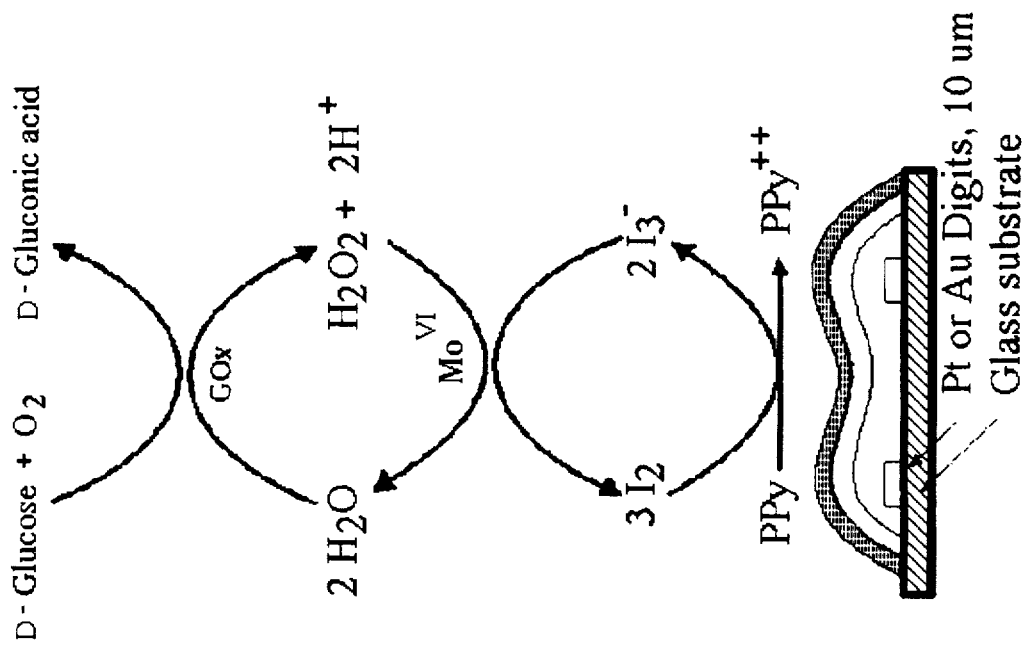
FIGS. 14A and 14B. Schematic illustration of a biotin-streptavidin capture immunosensor a) illustrating the binding reaction, and b) showing the chemistry of the sensor response reaction.
Figure 14A:
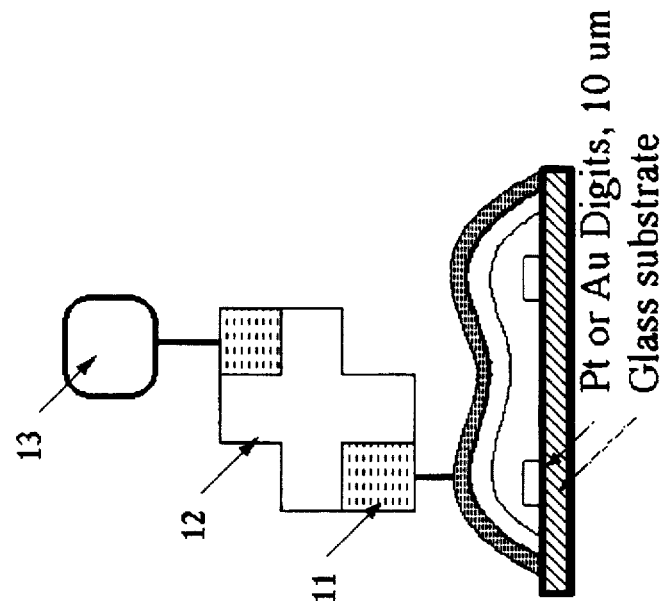

Polypyrrole-based glucose biosensors show a clear response to glucose in the concentration range 0.1 mM to 1.0 mM in a background of 0.05 M PBKCl at pH =7.2 and 1.0 mM KI at 20° C. Unlike for $H_2O_2$, the individual response curves rise following an induction period that follows INITIALIZATION and reveal time dependent changes in electrical conductivity during INTERROGATION using the discontinuous, small-amplitude voltage pulses of EPSIS. The slope of the response curve at $t_0$ gives the initial rate, a kinetic response parameter, determined by the activity of $H_2O_2$ and accordingly the activity of glucose. The initial responses obtained over the first 30 seconds at each concentration of glucose yields the initial rate curve. A plot of the initial rate parameter or slope versus concentration of glucose gives the calibration curve shown in FIG. 13. These results suggest a sensitivity that corresponds to almost a decade of conductivity change per decade of concentration. By using an oxidoreductase enzyme as a label that is conjugated to an antibody, several immunodiagnostic formats may be developed for immunosensors based on electroconductive polymers.

EXAMPLE 3

Biotin-Streptavidin Capture Immunosensor

Transducer Fabrication: Transducers were fabricated as previously described. Glucose-labeled biotin-streptavidin biosensors were fabricated from transducers by the growth and deposition of an electroconductive polymer layer possessing an inorganic catalyst that rendered the transducer sensitive to $H_2O_2$ and a biospecifc layer that possessed immobilized biotin that rendered the sensor specific to streptavidin binding. A glucose oxidase-biotin (GOx-Biotin or biotinylated glucose oxidase) conjugate was prepared which when bound to biotinimmobilized streptavidin resulted in a glucose sensitive response that depended on the available biotin-immobilized streptavidin-biotin binding. As indicated in Example 2 other oxidoreductase enzyme labels may also be used in this reaction scheme. The $H_2O_2$ produced in the substrate (glucose) initiated enzyme reaction reacts with the underlying $H_2O_2$-sensitive sensor to produce a conductimetric response that is determined by the concentration of glucose.

Membrane films were grown by potentiostatic electropolymerization onto the interdigit areas of chemically modified and derivatized prototransducers. The film grew on each electrode and also between the digits of the pair of electrodes such that it formed an adherent and fully contiguous membrane on the device. The film was grown from three different electropolymerization baths to form a three layer laminate membrane. The first was a highly conducting layer that was specifically attached via surface copolymerization with immobilized ω-pyrrolyl moieties. The second was a catalyst carrying layer that was directly polymerized onto the first and was covalently linked to it. The third was a biospecific layer possessing biotinylated poly(1-lysine) which was occluded with the polypyrrole during electropolymerization and a biotin linked 3-(1-pyrrolyl)propionic acid which was directly co-electropolymerized onto the second layer and was accordingly covalently linked to it. The first electropolymerization bath contained 0.2M pyrrole (Py), 2.5 mM poly(styrenesulfonic acid) (PSSA), and 2.5 mM sodium dodecylbenzenesulfonate (DBS) at a pH of 3.0 and at a constant T=20° C. Films were grown to a total anodic electropolymerization charge density, $Q_e$, of $2.5 \times 10^{-2}$ $C/cm^2$. The subsequent catalytic polymer layer was similarly prepared to a total anodic electropolymerization charge density, $Q_e$, of $1.00 \times 10^{-2}$ $C/cm^2$ from an electropolymerization bath that was neutralized by the dropwise addition of 0.015% polyvinylamine (PVAm) and also contained 1 mg/ml poly(1-lysine) and 0.1 mM $Mo_7O_{24}^{-6}$ ($Mo^{VI}$). The third layer was similarly prepared to a total anodic electropolymerization charge density, $1.00 \times 10^{-2}$ C/cm² from an electropolymerization bath that was neutralized by the dropwise addition of 0.015% polyvinylamine (PVAm) and also contained 0.5 mg/ml of biotinylated poly(1-lysine) and as well as 0.1M biotin-linked 3-(1-pyrrolyl)propionic. The biotin-linked 3-(1-pyrrolyl)propionic acid was prepared using the previously described carbodiimide linking chemistry. Biotinylated poly(1-lysine) was prepared by reaction of the free amine of poly(1-lysine) with NHS-LC-Biotin (Pierce) at a pH of 8.5.

Sensor Testing was performed using EPSIS in response to a sandwich binding format of immobilized-biotin|streptavidin|biotinylated glucose oxidase that was initiated by the addition of glucose in an aqueous background of 0.5M PBKCl pH 7.2 buffer containing 1.0 mM KI. FIG. 12a is a schematic illustration of the biotin-streptavidin capture electroconductive polypyrrole-based sensor. The assembled transducer is illustrated in FIG. 12b and comprises the electroconductive polymer component of the sensor, the platinized platinum counter electrode, and the Ag°/AgCl reference electrode. The sensor interrogation conditions used by EPSIS were as follows: Initialization Potential: −800 mV; Initialization Period: 3 min.; Pulse Voltage: 15 mV; Pulse Duration: 50 ms; Delay Time: 500 ms; No. of Cycles: 327 (ca. 180 sec). In these sensor response measurements, biotin-streptavidin capture biosensors were first electrolyzed away from their poise potential during initialization and then subsequently immediately interrogated for a total of 327 cycles or ca. 180 sec. The measured dynamically changing conductance multiplied by the cell constant of the device gave the sensor response profile.

Polypyrrole-based, glucose-labeled, biotin-streptavidin capture sandwich binding immunosensors show a clear response to glucose through the action of the glucose oxidase label that is captured in the biotin-streptavidin complex. The individual response curves rise following an induction period that follows INITIALIZATION and reveal time dependent changes in electrical conductivity during INTERROGATION using the discontinuous, small-amplitude voltage pulses of EPSIS. The slope of the response curve at $t_o$ gives the initial rate, a kinetic response parameter, determined by the activity of $H_2O_2$ and accordingly the activity of glucose. The initial responses obtained over the first 30 seconds upon addition of 10 mM glucose gives the response curve at a given extent of binding of biotin-streptavidin. These results suggest a biotin-streptavidin capture bioassay that exploits the use of glucose oxidase as a label. By using an oxidoreductase enzyme as a label that is conjugated to an antibody, several immunodiagnostic formats may be developed for immunosensors based on electroconductive polymers. This includes competitive and homogeneous immunodiagnostic formats. Some such formats may directly immobilize the antibody to the surface of the sensor or may directly immobilize the target analyte or hapten.

The foregoing invention has been described in considerable detail and by way of examples for the purpose of clarity and understanding, it will be readily appreciated by those with ordinary skill in the art, in light of teachings of this invention, that changes and modifications may be made thereto with departing from the spirit and scope of the appended claims.

What is claimed is:

1. A sensor comprising:

a microfabricated chip comprising at least one interdigitated microsensor electrode array, a first electrode of platinized platinum, and a second reference electrode, said first electrode and second reference electrode being coplanar on the chip with said array, said chip further comprising, an interdigit area that is chemically modified and derivatized to promote adhesion over said interdigitated electrode array, a first layer of electroactive polymer material formed over the interdigit area, and being covalently attached, adhered, and contiguous with the interdigit area of the chip, a second layer of electroactive polymer material, including an inorganic catalyst, formed over said first electroactive polymer layer, and a third layer of electroactive polymer material, including an indicator agent, formed over said second electroactive polymer layer.

2. The sensor of claim 1 wherein said sensor comprises a chemical sensor.

3. The sensor of claim 1 wherein said sensor comprises a biological sensor.

4. The sensor of claim 1 wherein said interdigitated microsensor electrode array comprises gold or platinum.

5. The sensor of claim 1 wherein the reference electrode comprises silver/silver chloride.

6. The sensor of claim 1 wherein said interdigit area is chemically modified using a functional silane which is subsequently derivatized with a polymerizable moiety of pyrrole, thiophene or aniline.

7. The sensor of claim 1 wherein said first electroactive polymer comprises polypyrrole, polythiophene or polyaniline.

8. A sensor of claim 1 comprising three interdigitated microsensor electrode arrays, each with line and space dimensions which range from about 2 to 20 µm, a platinized platinum counter electrode having an area of at least 10 times the area of the interdigitated microsensor electrode array, and a reference electrode of chloridized silver/silver chloride (Ag°/AgCl).

9. A sensor of claim 1 wherein the interdigitated microsensor electrode array comprises ten (10) opposing digit pairs, each digit being about 2.999 mm long with 10 µm line and space dimensions.

10. The sensor of claim 1 wherein the interdigit areas are chemically modified with 3-aminopropyltrimethoxysilane and the free primary amine derivatized by direct linking of the 1° amine of the silane to the carboxylic acid group of 3-(1-pyrrolyl)propionic acid.

11. The sensor of claim 1 wherein the inorganic catalyst is drawn form the class containing $Mo_7O_{24}^{6-}$($Mo^{VI}$).

12. The sensor of claim 1 in which the indictor agent is drawn from the class containing enzymes or member of a specific binding pair reagent.

13. A chemical sensor comprising:

a microfabricated chip comprising a plurality of interdigitated microsensor electrode arrays, a first electrode of platinized platinum, and a second reference electrode, said first electrode and second reference electrode being coplanar on the chip with said arrays, said chip further comprising, an interdigit area that is chemically modified with a functional silane and derivatized to promote adhesion over said interdigitated electrode arrays, a first layer of electroactive polymer material formed over the interdigit area, and being covalently attached, adhered, and contiguous with the interdigit area of the chip, a second layer of electroactive polymer material, including an inorganic catalyst, formed over said first electroactive polymer layer, and a third layer of electroactive polymer material, including an indicator agent, formed over said second electroactive polymer layer.

14. A biological sensor comprising:

a microfabricated chip comprising a plurality of interdigitated microsensor electrode arrays, a first electrode of platinized platinum, and a second reference electrode, said first electrode and second reference electrode being coplanar on the chip with said array, said chip further comprising, an interdigit area that is chemically modified and derivatized to promote adhesion over said interdigitated electrode array, a first layer of electroactive polymer material formed over the interdigit area, and being covalently attached, adhered, and contiguous with the interdigit area of the chip, a second layer of electroactive polymer material, including an inorganic catalyst, formed over said first electroactive polymer layer, and a third layer of electroactive polymer material, including an indicator agent, formed over said second electroactive polymer layer.

* * * * *